(12) United States Patent
Lipson

(10) Patent No.: US 9,587,016 B2
(45) Date of Patent: Mar. 7, 2017

(54) TREATMENT METHOD FOR LUNG REMODELING DISEASES

(71) Applicant: FibroGen, Inc., San Francisco, CA (US)

(72) Inventor: Kenneth E. Lipson, San Mateo, CA (US)

(73) Assignee: FIBROGEN, INC., San Francisco, CA (US)

(*) Notice: Subject to any disclaimer, the term of this patent is extended or adjusted under 35 U.S.C. 154(b) by 0 days.

(21) Appl. No.: 14/741,747

(22) Filed: Jun. 17, 2015

(65) Prior Publication Data
US 2015/0376270 A1 Dec. 31, 2015

Related U.S. Application Data

(63) Continuation of application No. 13/883,521, filed as application No. PCT/US2011/059589 on Nov. 7, 2011, now abandoned.

(60) Provisional application No. 61/456,370, filed on Nov. 5, 2010.

(51) Int. Cl.
| | | |
|---|---|---|
| *A61K 39/395* | (2006.01) | |
| *C07K 16/22* | (2006.01) | |
| *A61K 45/06* | (2006.01) | |
| *A61K 39/00* | (2006.01) | |

(52) U.S. Cl.
CPC ......... *C07K 16/22* (2013.01); *A61K 39/3955* (2013.01); *A61K 45/06* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,492,129 B1 | 12/2002 | Grotendorst | |
| 7,115,390 B1 | 10/2006 | Grotendorst et al. | |
| 7,405,274 B2 | 7/2008 | Lin et al. | |
| 7,871,617 B2 * | 1/2011 | Lin | C07K 16/22 424/133.1 |
| 8,642,034 B2 * | 2/2014 | Streisand | 424/133.1 |
| 2003/0113816 A1 | 6/2003 | Weitz et al. | |

FOREIGN PATENT DOCUMENTS

| | | | |
|---|---|---|---|
| WO | WO 96/38172 A1 | 12/1996 | |
| WO | WO 00/35936 A1 | 6/2000 | |
| WO | WO 03/053340 A1 | 7/2003 | |
| WO | WO 2008/070117 | * 6/2008 | |
| WO | WO 2009/026428 A1 | 2/2009 | |
| WO | WO 2011/056234 A1 | 5/2011 | |

OTHER PUBLICATIONS

Ahmed, M.S., et al., "Induction of Pulmonary Connective Tissue Growth Factor in Heart Failure is Associated With Pulmonary Parenchymal and Vascular Remodeling," Cardio. Res. (2007) 74:323.333.
Bhatt, N., et al., "Promising Pharmacologic Innovations in Treating Pulmonary Fibrosis," Current Opin in Pharm. (2006) 6:284-292.
Guha, M., "Specific Down-Regulation of Connective Tissue Growth Factor Attenuates Progression of Nephropathy in Mouse Models of Type 1 and Type 2 Diabetes," FASEB Jour. (2007) 21:1-14.
Kondo, S., et al., "Characterization of a Mouse tgf 3'-UTR Segment That Mediates Repressive Regulation of Gene Expression," Biochem. & Biophys, Res. Comm. (2000) 278:119-124.
Kothapalli, D., "Transforming Growth Factor B Induces Anchorage-Independent Gwoth of NRK Fibroblasts via a Connective Tissue Growth Factor-Dependent Signaling Pathway," Cell Growth & Differ. (1997), vol. 8: 61-68.
Lai, T.-C., et al., "Small Interfering RNAs (siRNAs) Targeting TGF-B1 mRNA Suppress Asbestos-Induced Expression of TGF-B1 and CTGF in Fibroblasts," J. Environ. Path. (2009) 28(2):109-119.
Li, C., et al., "Role of Connective Tissue Growth Factor (IGFBP-8) in Radiation-Induced Lung Fibrosis (RILF)," Inter. Jour. Rad. Oncol. (2008) vol. 72, No. 1 (Abstract).
Ostrau, C., et al., "Lovastatin Attenuates Ionizing Radiation-Induced Normal Tissue Damage In Vivo," Radio, & Oncol. (2009) 92:492-499.
Ponticos, M., et al., "Pivotal Role of Connective Tissue Growth Factor in Lung Fibrosis," Arthritis & Rheumat. (2009) vol. 60, (7):2142-2155.
Shimo, T., "Inhibition of Endogenous Expression of Connective Tissue Growth Factor by Its Antisense Oligonucleotide and Antisense RNA Suppresses Proliferation and Migration of Vascular Endothelial Cells," J. Biochem (1998) 124:130-140.
Thannickal, V., et al., "Idiopathic Pulmonary Fibrosis: Emerging Concepts on Pharmacotherapy," Expert Opin. Pharmacosher. (2004) 5(8):1671-1686.
Uchio, K., et al., "Down-Regulation of Connective Tissue Growth Factor and Type 1 Collagen mRNA Expression by Connective Tissue Growth Factor Antisense Olignocleotide During Experimental Liver Fibrosis" Woudn Repair Regen (2004) : 60-66.

(Continued)

*Primary Examiner* — Marianne P Allen
(74) *Attorney, Agent, or Firm* — FibroGen, Inc.; Leanne C. Price; Paul Borchardt

(57) ABSTRACT

The present invention relates to methods and medicaments useful for pre-treatment, treatment, or amelioration of lung remodeling disease. Methods and medicaments for reducing, preventing, or reversing increased lung density, improving lung function, and increasing survivability in subjects having lung remodeling disease are also provided.

4 Claims, 11 Drawing Sheets

(56) References Cited

OTHER PUBLICATIONS

Williams, J.A., et al., "Effect of Administration of Lovastatin on the Development of Late Pulmonary Effects after Whole-Lung Irradiation in a Murine Model," Rad. Res. (2004) 151:560-567

Bickelhaupt, S., et al., "Attenuation and Reversal of Radiation-Induced Pulmonary Fibrosis in a Murine Model by an Anti-CTGF Monoclonal Antibody," Int. J. Radiat. Oncol. (2010) 78:Suppl. (Abstract).

\* cited by examiner

TREATMENT METHOD FOR LUNG REMODELING DISEASES

This application is a continuation of U.S. application Ser. No. 13/883,521 filed 29 Jan. 2014, which claims benefit of International Application No. PCT/US2011/059589 filed 7 Nov. 2011, which claims the benefit of U.S. Provisional Application Ser. No. 61/456,370, filed on 5 Nov. 2010, which are hereby incorporated by reference in their entirety.

FIELD OF THE INVENTION

The present invention relates to methods and medicaments useful for treatment of lung remodeling diseases. Methods and medicaments for improving lung function, reducing lung inflammation, and increasing survivability in subjects having a lung remodeling disease are also provided.

BACKGROUND

Lung remodeling diseases (LRD) are a group of disorders that lead to progressive loss of function in the alveoli. Although the disease typically involves an initial acute inflammatory response, many patients do not seek treatment until the disease has progressed to a more advanced chronic phase. LRD may be due to a number of different underlying factors. Exposure to occupational or environmental inhalants, including inhalation of organic dust, inorganic dust, cigarette smoke or noxious gases can often result in LRD. First line treatment requires identification and removal of the causative agent from the patient's environment. LRD can also be caused by exposure to certain drugs or ionizing radiation, as may occur during chemo- or radiation therapy in cancer patients. LRD may also result from an exaggerated immune response, such as in sarcoidosis, or part of a more systemic collagen vascular disorder. In many cases, the underlying cause of LRD remains unknown.

Although the initiating agent(s) or circumstances may vary, the immunopathogenic response of lung tissues generally involves a similar course of events. The initial response is inflammation of the air spaces and alveolar walls, causing an acute alveolitis. If the condition persists, inflammation spreads to the interstitium and vasculature of the alveoli. At early stages, the alveolar and adjacent capillary endothelial cells become leaky, leading to alveolar and septal edema, and the number of immune cells found in bronchoalveolar lavage (BAL) fluid and/or sputum increases. In particular, the number of polymorphonuclear leukocytes (PMNs), which normally comprise about 1-3% of the cellular component of BAL and/or sputum, can increase to 20% or more. Persistence in the inflammatory response leads to desquamation of the wall of the alveoli and compensatory proliferation of fibroblast in the interstitium. The resultant scarring of lung tissue leads to significant alterations in gas exchange and ventilatory function. LRD can also involve the bronchioles, and patients may present with bronchiolitis.

Current treatment options for LRD are limited and do not provide long-term improvement in most patients. Corticosteroids such as prednisone are often provided to reduce the inflammation associated with LRD. However, immunosuppressant therapy can lead to increased infection in the compromised lung and a worsening of the condition. As the treatment options for patients with lung remodeling disease are inadequate, new methods and medicaments for the treatment of lung remodeling disease are therefore desirable.

SUMMARY OF THE INVENTION

In one embodiment, the present invention provides a method of treating a lung remodeling disease in a subject, the method comprising administering to the subject an anti-connective tissue growth factor (anti-CTGF) agent, thereby treating the lung remodeling disease. In another embodiment, the present invention provides a method for pre-treating a subject at increased probability of being afflicted with a lung remodeling disease to prevent or reduce a resulting pathological feature of the lung remodeling disease, the method comprising administering to the subject an anti-CTGF agent, thereby preventing or reducing a resulting pathological feature of lung remodeling disease. In some embodiments, the anti-CTGF agent is selected from the group consisting of antibodies, antibody fragments, antibody mimetics, antisense oligonucleotides, siRNA, miRNA, ribozymes, aptamers and small molecules. In a preferred embodiment, the anti-CTGF agent for use in these methods is an antibody that binds specifically to connective tissue growth factor (CTGF). In particular embodiments, the anti-CTGF agent is an antibody that has the same amino acid sequence as the antibody produced by the cell line identified by ATCC Accession No. PTA-6006, or is an antibody that binds to CTGF competitively with an antibody produced by the cell line identified by ATCC Accession No. PTA-6006.

Evidence is now presented that use of an anti-CTGF agent is effective to treat various lung remodeling diseases. The results from a radiation-induced lung injury model, typified by an acute inflammatory response and a later chronic response that features a progressive increase in lung density and lung remodeling (e.g., septal thickening), show that treatment with anti-CTGF agents is effective to halt and, in some circumstances, reverse the increases in lung density. Results from a neonatal hyperoxemia model, typified by reduced alveolarization and vascularization in the lungs, show that treatment with anti-CTGF agents is effective to prevent or attenuate a reduction in alveolarization and vascularization. Both models exhibit pathological remodeling in the lung, although the remodeling manifests differently with different results. The method of the present invention using anti-CTGF agents is effective to treat these different manifestations of lung remodeling. In further embodiments, the methods of the invention are effective in preventing, reducing or reversing destruction of alveoli in a subject in need thereof by administering to the subject an effective amount of an anti-connective tissue growth factor (anti-CTGF) agent, thereby preventing, reducing or reversing destruction of alveoli. In additional embodiments, the methods of the invention are effective in increasing alveolarization in a subject in need thereof by administering to the subject an effective amount of an anti-connective tissue growth factor (anti-CTGF) agent, thereby increasing alveolarization. In other embodiments, the methods of the invention are effective in increasing or preserving pulmonary vascularization in a subject in need thereof by administering to the subject an effective amount of an anti-connective tissue growth factor (anti-CTGF) agent, thereby increasing or preserving pulmonary vascularization.

The present invention provides methods and medicaments for treatment of lung remodeling disease. The present invention also provides methods and medicaments for pre-treating an individual that has an increased probability of being afflicted with lung remodeling disease, thereby preventing or reducing the severity of a subsequent lung remodeling disease. In some embodiments the lung remodeling disease is selected from the group consisting of asthma, chronic bronchitis, chronic obstructive pulmonary disease (COPD), sarcoidosis, hypersensitivity pneumonitis, collagen-vascular disease, eosinophilic granuloma, nonspecific interstitial pneumonitis, respiratory bronchiolitis-associated interstitial lung disease, desquamative interstitial pneumonitis, lymphocytic interstitial pneumonitis, acute interstitial pneumonitis, bronchopulmonary dysplasia, hypersensitivity pneumonitis, asbestosis, bauxite fibrosis, beryliosis, byssinosis, coal worker's pneumoconiosis, cork worker's lung, farmer's lung, pigeon breeder's lung, silo filler's disease, mushroom worker's lung, Labrador Lung disease, siderosis, silicosis and silicosiderosis, Caplan's syndrome, high-altitude pulmonary edema, aspiration pneumonia, drug-induced pulmonary toxicity, lymphangioleiomyomatosis, bronchiolitis obliterans (BOS), pediatric respiratory distress syndrome, acute respiratory distress syndrome, hyperoxia-induced bronchopulmonary dysplasia, cystic fibrosis and lung remodeling associated with pulmonary hypertension and pulmonary venoocclusive disease.

In one embodiment, the present invention provides methods for treatment of lung remodeling disease in a subject, wherein the method comprises administering to the subject an anti-connective tissue growth factor (anti-CTGF) agent. In another embodiment, the present methods can be used to pre-treat a subject at increased probability of being afflicted with lung remodeling disease. The methods of the present invention prevent, reduce, stabilize, reverse or normalize various pathological features of lung remodeling disease. Such pathological features include, but are not limited to, decreased lung volume, decreased potential air space, increased lung density, presence of remodeled lung tissue, increased septal thickness, decreased alveolarization, decreased pulmonary vascularization, increased medial wall thickness, decreased formation or presence of secondary septa, increased right ventricular systolic pressure (RVSP), increased right ventricular hypertrophy (RVH), decreased $PaO_2$ (arterial pressure of oxygen), increased lung volume, increased presence of polymorphonuclear leukocytes (PMNs) in bronchoalveolar lavage (BAL) fluid and/or sputum, the presence of inflammation and the presence of pulmonary edema. Other pathological features of lung remodeling diseases are well known and are included here.

Thus, in one embodiment, the present methods provide a method of reducing, stabilizing, reversing or normalizing a pathological feature associated with lung remodeling disease in a subject, the method comprising administering to the subject an anti-CTGF agent, thereby reducing, stabilizing, reversing or normalizing the pathological feature of lung remodeling disease. In another embodiment, the present invention provides a method for pre-treating a subject at increased probability of being afflicted with lung remodeling disease to prevent or reduce a resulting pathological feature of lung remodeling disease, the method comprising administering to the subject an anti-CTGF agent, thereby preventing or reducing a resulting pathological feature of lung remodeling disease. In various embodiments, the pathological feature of lung remodeling disease is selected from the group consisting of decreased lung volume, decreased potential air space, increased lung density, presence of remodeled lung tissue, increased septal thickness, decreased alveolarization, decreased pulmonary vascularization, increased medial wall thickness, decreased formation or presence of secondary septa, increased right ventricular systolic pressure (RVSP), increased right ventricular hypertrophy (RVH), decreased $PaO_2$, increased lung volume, increased presence of polymorphonuclear leukocytes (PMNs) in bronchoalveolar lavage (BAL) fluid and/or sputum, the presence of inflammation and the presence of pulmonary edema.

Therefore, in one embodiment, the present invention provides a method of preventing or stabilizing lung density in a subject having pathologically changed lung density due to lung remodeling disease, the method comprising administering to the subject an anti-CTGF agent, thereby preventing or stabilizing lung density in the subject. In another embodiment, the present invention provides a method of reducing or normalizing a pathological change in lung density in a subject at increased probability of being afflicted with lung remodeling disease, the method comprising administering to the subject an anti-CTGF agent, thereby reducing or normalizing a pathological change in lung density in the subject. Lung density may be measured by any method known to one of skill in the art. In one particular aspect, the lung density is measured using lung images from computed tomography (CT) scans; more particularly, from high resolution CT (HRCT) scans. In some embodiments, the subject having increased lung density has a lung density of −500 to +100 Hounsfield Units (HU). In other embodiments, the subject having increased lung density has a lung density of −500 to −100 HU. In still other embodiments, the subject having increased lung density has a lung density of −500 to −300 HU. Normal healthy human lung density varies but typically is in the range of −800 to −900 HU. Subjects having a LRD may have a lung density that varies substantially from the normal and may be either more or less dense than the normal. For example, a subject having a radiation-induced lung disorder, e.g., radiation pneumonitis, may have a lung density that is higher than normal e.g., a LD of >−800 HU, or >−750 HU, or >−700 HU, while a subject having a LRD that is characterized by airway remodeling, e.g., COPD or emphysema, may have a LD that is lower than normal, e.g a LD of <−900 HU, or <−910 HU, or <−950 HU. The methods of the present invention are effective to normalize the lung density (i.e., return the LD closer to the normal range or to within the normal range) in a subject having abnormal lung density as a result of a LRD. In some cases, such normalizing will bring about a decrease in lung density in a subject with increased lung density. In other cases, such normalizing will bring about an increase in lung density in a subject with decreased lung density.

In some embodiments, the patient's lung density is measured prior to treatment. The measured lung density can be compared to a standard lung density range and if the lung density is denser than the standard lung density range, treatment with an anti-CTGF agent can be initiated. In other embodiments, the patient's lung density is measured after treatment. The measured density can be compared to a standard lung density range and if the lung density is denser than the standard density range, treatment can be repeated as necessary to normalize the patient's lung density.

In another embodiment, the present invention provides a method of reducing, stabilizing, reversing or normalizing lung remodeling in a subject having lung remodeling disease, the method comprising administering to the subject an anti-CTGF agent, thereby reducing, stabilizing, reversing or normalizing lung remodeling in the subject. In another embodiment, the present invention provides a method of preventing or reducing lung remodeling in a subject at increased probability of being afflicted with lung remodeling disease, the method comprising administering to the subject an anti-CTGF agent, thereby preventing or reducing lung remodeling in the subject. Lung remodeling may be measured by any method known to one of skill in the art. In some embodiments, lung remodeling is measured by lung imaging from CT scans; more particularly, from HRCT. In other embodiments, lung remodeling is measured by lung biopsy and histology. In some embodiments, lung remodeling is measured as a change in potential airspace in lung tissue. In particular embodiments, the subject having a lung remodeling disease has decreased potential airspace in lung tissue relative to normal. In other embodiments, lung remodeling is measured by percentage of lung showing honeycomb changes or fibroblastic foci on lung images. In particular embodiments, the subject having lung remodeling disease has increased percentage of honeycomb change or fibroblastic foci in lung images.

In some embodiments, the presence and extent of lung remodeling is determined after measuring at least one functional lung parameters selected from the group consisting of vital capacity (VC), residual volume (RV), forced expiratory volume (FEV), forced vital capacity (FVC), forced expiratory flow (FEF), maximum flow (Vmax), peak expiratory flow rate (PEFR), inspiratory reserve volume (IRV), functional residual capacity (FRC), inspiratory capacity, total lung capacity (TLC), expiratory reserve volume (ERV), tidal volume and maximum voluntary ventilation (MVV). The patient's values can then be compared against standard lung function parameters for diagnosing the presence and extent of the lung remodeling disease. In other embodiments, treatment with an anti-CTGF agent improves one or more functional lung parameters.

The measurement of a subject's $PaO_2$, diffusing capacity of the lung for CO (DLCO), or percent oxygen saturation of blood are also useful in assessing lung function because typically reduced values for functional lung parameters result in lower $PaO_2$, DLCO or percent oxygen saturation of blood values. Treatment with an anti-CTGF agent can increase the $PaO_2$, DLCO or percent oxygen saturation of blood values of a patient with a lung remodeling disease. In particular embodiments, improved lung function increases or normalizes a patient's $PaO_2$. In various embodiments, the methods of the present invention are used to treat a subject having a $PaO_2$ of below 80 mmHg, particularly below 75 mmHg, and more particularly below 70 mmHg.

Measurement of one or more lung function parameters, $PaO_2$, DLCO or percent oxygen saturation of blood values can be measured prior to treatment in a patient suspected of having a lung remodeling disorder and compared to one or more standard values to form the basis of a diagnosis. Treatment can be initiated if the measured lung function parameters, $PaO_2$, DLCO or percent oxygen saturation of blood values are appreciable outside a standard range of values, i.e., at least 5%, 10%, 15%, 20%, 25%, 30%, 40% or 50%. Further, treatment response can be monitored by measuring one or more lung function parameters of $PaO_2$, DLCO or percent oxygen saturation of blood values after treatment and comparing the measured lung function parameters to standard lung function parameters. An increase or normalization in one or more lung function parameters, $PaO_2$, DLCO or percent oxygen saturation of blood values indicate that the treatment is efficacious. The administration of the anti-CTGF agent can be repeated if the measured lung function parameters, $PaO_2$, DLCO or percent oxygen saturation of blood values are below a desired range or appreciable outside of the standard range of values for the lung function parameters, i.e., at least 5%, 10%, 15%, 20%, 25%, 30%, 40% or 50%.

In additional embodiments, the presence and extent of a lung remodeling disease is measured by the cell count and cellular composition of BAL fluid and/or sputum. In some embodiments, the methods of the invention reduce or normalize the cellular make-up of BAL fluid and/or sputum. In various embodiments, the methods of the present invention are used to treat a subject having an elevated percentage of PMNs in BAL fluid and/or sputum with the methods of the invention reducing the percentage of PMNs in BAL fluid and/or sputum. In particular embodiments, the subject has greater than 5% PMNs in BAL fluid and/or sputum, particularly greater than 10%, and more particularly greater than 15%. In particular embodiments, the cell count and cellular composition of BAL fluid and/or sputum is normalized over the treatment time course.

In other embodiments, the presence and extent of a lung remodeling disease is measured by the presence and extent of pulmonary edema or cellular infiltration of lung tissue. In certain instances, edema and/or cellular infiltration is an acute event, while in other instances the edema and/or cellular infiltration is a chronic event. Typically, cellular infiltration is associated with the proliferation of leukocytes. In some embodiments, the methods of the present invention prevent, reduce or reverse pulmonary edema, cellular infiltration and/or cellular proliferation.

In yet another embodiment, the present invention provides a method of increasing the likelihood of survival in a subject having lung remodeling disease, the method comprising administering to the subject an anti-CTGF agent, thereby increasing the likelihood of survival in the subject.

In various embodiments, the subject is an individual, preferably a mammal, more preferably a human, who has lung remodeling disease. In other embodiments, the subject is an individual, preferably a mammal, more preferably a human, who is at increased probability of being afflicted with lung remodeling disease. In certain embodiments, the subject's probability of being afflicted with lung remodeling disease is due to an occupational exposure to an inhalant or particulate suspected of causing lung remodeling disease. Such inhalants or particulates may include, but are not limited to, asbestos, organic dust, inorganic dust or smoke inhalation. In certain embodiments, the subject's probability of being afflicted with lung remodeling disease is due to occupational, environmental, or therapeutic exposure to ionizing radiation. Such exposure may be due to, e.g., radiation therapy or nuclear medicine treatments.

In some embodiments, the methods are initiated upon diagnosis of lung remodeling disease in a subject. In various embodiments, the methods may be initiated prior to an event associated with increased probability of being afflicted with lung remodeling disease. Such an event may be an occupational event, e.g., potential exposure to asbestos as part of an asbestos abatement project; or a medical event, e.g., exposure to ionizing radiation as part of radiation therapy. The method may be applied at appropriate intervals to achieve improvement in a pathological feature of lung remodeling disease and/or lung function as measured by any of the parameters provided herein. In particular embodiments, the methods may be applied 1, 2, 3, 4, or 5 time(s) or more per month. In some embodiments, the methods are applied 1 time per week or 1 time every other week. In various embodiments, the methods are continued until the pathological feature or functional parameter is essentially normalized or the subject is no longer considered at risk.

The methods of the invention are accomplished by administering to the subject in need an anti-CTGF agent or a medicament comprising an anti-CTGF agent. In particular embodiments the anti-CTGF agent is an antibody that binds specifically to CTGF, or a polynucleotide inhibitor of CTGF expression (for example, an antisense oligonucleotide, siRNA, shRNA, or miRNA). In a preferred embodiment, the anti-CTGF agent is an antibody that binds specifically to CTGF. In various embodiments, the antibody is an antibody described and claimed in U.S. Pat. No. 7,871,617. In particular embodiments, the antibody has the amino acid sequence of the antibody produced by the cell line identified by ATCC Accession No. PTA-6006. In other embodiments, the antibody competitively binds to CTGF with an antibody produced by ATCC Accession No. PTA-6006. A particular antibody for use in the present methods is CLN1 or mAb1 as described in U.S. Pat. No. 7,405,274, or an antibody substantially equivalent thereto or derived therefrom.

In another aspect, the present invention provides medicaments for treating lung remodeling disease. In one embodiment, the present invention provides the use of an anti-CTGF agent in preparing a medicament for preventing, stabilizing or reversing a pathological change in lung density in a subject having lung remodeling disease. In another embodiment, the present invention provides the use of an anti-CTGF agent in preparing a medicament for preventing, stabilizing or reversing decreased alveolarization in a subject having lung remodeling disease. In another embodiment, the present invention provides the use of an anti-CTGF agent in preparing a medicament for attenuating lung remodeling in a subject having lung remodeling disease. The medicament may be used to treat, prevent, reduce, reverse, normalize, and/or stabilize various pathological features of lung remodeling disease. Such features include, but are not limited to, decreased lung volume, increased lung density, remodeled lung tissue, decreased alveolarization, decreased vascularization in the lung. Any anti-CTGF agent that directly inhibits the expression or activity of CTGF may be used in formulating the present medicaments. In particular embodiments the anti-CTGF agent is an antibody that binds specifically to CTGF, or a polynucleotide inhibitor of CTGF expression (for example, an antisense oligonucleotide, siRNA, shRNA, or miRNA). In a preferred embodiment, the anti-CTGF agent is an antibody that binds specifically to CTGF. Any antibody that binds specifically to CTGF may be used in formulating the present medicaments. In various embodiments, the antibody for use in the present medicaments is an antibody described and claimed in U.S. Pat. No. 7,871,617, which application is incorporated in its entirety by reference herein. In particular embodiments, the antibody has the amino acid sequence of the antibody produced by the cell line identified by ATCC Accession No. PTA-6006. In other embodiments, the antibody competitively binds to CTGF with an antibody produced by ATCC Accession No. PTA-6006. A particular antibody for use in the present medicaments is CLN1 or mAb1 as described in U.S. Pat. No. 7,405,274, or an antibody substantially equivalent thereto or derived therefrom.

The anti-CTGF agent can be administered systemically or directly to the lungs as a particulate, aerosol or nebulized solution. In further embodiments, in addition to the anti-CTGF agent, the subject also administered a therapeutic agent selected from the group consisting of corticosteroids, bronchodilators, anticholinergics, vasodilators, diuretics, anti-hypertensive agents, acetazolamide, antibiotics, immunosuppressive drugs, surfactants, supplemental oxygen and mechanical ventilation.

These and other embodiments of the present invention will readily occur to those of skill in the art in light of the disclosure herein, and all such embodiments are specifically contemplated.

BRIEF DESCRIPTION OF THE DRAWINGS

FIG. 1A provides a schematic of the different dosing schedules exemplified for the present methods and medicaments following an initial insult, i.e., exposure to ionizing radiation. FIG. 1B sets forth the typical course of leukocyte infiltration following initial insult. FIG. 1C sets forth the typical course of edema and fibrosis following initial insult. FIG. 1D sets forth the change in lung density following initial insult.

FIG. 2A sets forth data for improved potential airspace when administration of the present methods or medicaments was initiated 2 days before or 2 days after the initial insult and continued for 8 weeks. FIG. 2B sets forth data for improved potential airspace when administration of the present methods or medicaments was initiated 20 days after the initial insult and continued for 8 weeks. FIG. 2C sets forth data for improved potential airspace when administration of the present methods or medicaments was initiated 112 days after the initial insult and continued for 8 weeks.

FIG. 3A sets forth data for reducing increased lung density when administration of the present methods or medicaments was initiated 2 days before or 2 days after the initial insult and continued for 8 weeks. FIG. 3B sets forth data for preventing increased lung density when administration of the present methods or medicaments was initiated 20 days after the initial insult and continued for 8 weeks. FIG. 3C sets forth data for preventing and/or reversing increased lung density when administration of the present methods or medicaments was initiated 112 days after the initial insult and continued for 8 weeks.

FIG. 4A sets forth blood partial oxygen pressure ($PaO_2$) at week 30 following the initial insult for animals that were untreated or treated with the methods and medicaments of the present invention. The striped box in the figure defines the normal range for $PaO_2$ in this model organism and demonstrates that treatment with an anti-CTGF agent can normalize $PaO_2$ values in treated animals. FIG. 4B plots blood $PaO_2$ and lung density at week 30 following the initial insult for animals that were untreated or treated with the methods and medicaments of the present invention, showing that improved lung function correlates inversely with lung density. The shaded region in the figure defines the normal oxygen saturation range in this model organism.

FIG. 5A sets forth data for increased survivability when administration of the present methods or medicaments was initiated 2 days before or 2 days after the initial insult and continued for 8 weeks. FIG. 5B sets forth data for increased survivability when administration of the present methods or medicaments was initiated 20 days after the initial insult and continued for 8 weeks. FIG. 5C sets forth data for increased survivability when administration of the present methods or medicaments was initiated 112 days after the initial insult and continued for 8 weeks.

DESCRIPTION OF THE INVENTION

Figure 1A:
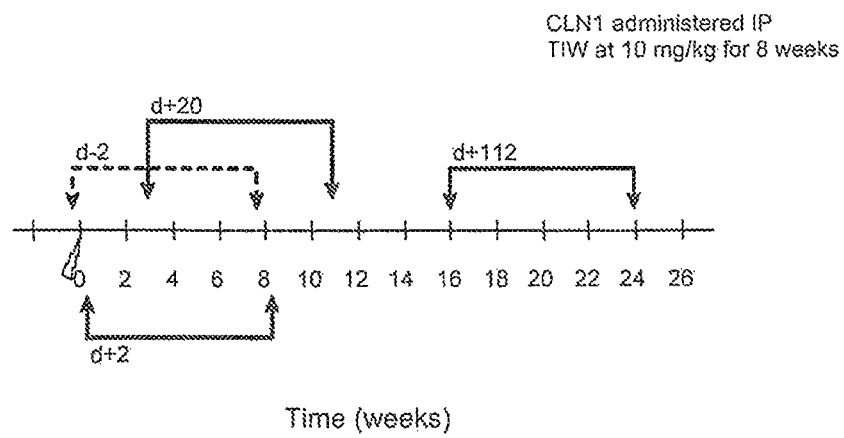
FIGS. 1A-1D set forth various aspects of an animal model of one type of lung remodeling disease.

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the present invention. Nothing herein is to be construed as an admission that the present invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

In one aspect, the present invention provides methods for treating lung remodeling disease. As used herein, "lung remodeling disease" or "LRD" refers to a group of lung diseases affecting the alveoli and interstitium that result in progressive scarring and loss of function. LRD may be caused by exposure to a number of toxins or pollutants including, but not limited to, inorganic dust such as silica or hard metal dust; asbestos fibers, noxious gases such as ammonia or chlorine gas; organic particles from various sources such as grain, sugar cane, and bird and animal droppings, moldy hay, and bacterial or fungal growths. LRD may also be caused by thoracic exposure to radiation or certain drugs such as chemotherapy drugs, various heart medications, certain psychiatric medications, and some antibiotics. In many cases, the cause of LRD is unknown and LRD is identified as idiopathic. Diagnosis of LRD is based on symptoms including dyspnea, nonproductive cough, fatigue, excessive mucus and/or sputum production, chest tightness, wheezing and low-grade fever; and generally involves blood tests, e.g., measurement of partial oxygen saturation of the blood; pulmonary function tests, e.g., measurement of total lung volume, residual volume, and vital capacity; and computed tomography (CT) scans of the thorax, e.g., to measure lung density and monitor lung remodeling.

Lung remodeling diseases (LRD) include diseases, disorders and pathological conditions in which pathological or maladaptive remodeling occurs in the lung tissues, including bronchi, bronchioles, alveoli, airways, interstitium and pulmonary vasculature. LRD can include airway diseases like asthma and chronic bronchitis and lung tissue diseases like sarcoidosis. Other lung remodeling diseases include interstitial lungs diseases, e.g., hypersensitivity pneumonitis, collagen-vascular disease, eosinophilic granuloma, nonspecific interstitial pneumonitis, respiratory bronchiolitis-associated interstitial lung disease, desquamative interstitial pneumonitis, lymphocytic interstitial pneumonitis, acute interstitial pneumonitis. Numerous lung remodeling diseases are associated with occupational exposure to particulates including asbestosis, bauxite fibrosis, beryliosis, byssinosis, coal worker's pneumoconiosis, cork worker's lung, farmer's lung, mushroom worker's lung; Labrador Lung disease, pigeon breeder's lung, siderosis, silicosis, silo filler's disease and silicosiderosis. Certain lung remodeling diseases are associated with autoimmune diseases including, collagen-vascular diseases, e.g., systemic lupus erythematosus, rheumatoid arthritis (Caplan's syndrome), progressive systemic sclerosis, scleroderma, dermatomyositis, polymyositis, ankylosing spondylitis, Sjögren syndrome and mixed connective-tissue disease, or genetic diseases e.g., cystic fibrosis and alpha-1 antitrypsin deficiency. Other lung remodeling diseases include bronchiectasis, emphysema, COPD; diseases associated with barotrauma and mechanical ventilation; high-altitude pulmonary edema, aspiration pneumonia, drug-induced pulmonary toxicity, lymphangioleiomyomatosis, lung transplantation rejection, e.g., bronchiolitis obliterans (BOS), pediatric and adult respiratory distress syndrome, hyperoxia-induced bronchopulmonary dysplasia, and remodeling associated with pulmonary hypertension and pulmonary venoocclusive disease.

In some embodiments, the subject in need of treatment is an individual, preferably a mammal, more preferably a human, who has been diagnosed with a lung remodeling disease. In other embodiments, the subject is an individual, preferably a mammal, more preferably a human, who is at increased probability or likelihood of being afflicted with a lung remodeling disease. In certain embodiments, the subject's probability or likelihood of being afflicted with a lung remodeling disease is due to exposure to an inhalant suspected of causing lung remodeling disease, as described supra. In other embodiments, the subject's probability or likelihood of being afflicted with lung remodeling disease is due to a treatment with a drug such as those described infra. In certain embodiments, the subject's probability or likelihood of being afflicted with lung remodeling disease is due to an underlying condition associated with LRD, e.g., systemic lupus erythematosus.

Lung remodeling diseases can be classified into three categories: lung remodeling diseases associated with a decrease in lung volume or a restriction in lung expansion; lung remodeling diseases associated with an increase in lung volume; and lung remodeling diseases associated with constricted or blocked airways. Frequently, a lung remodeling disease will feature both a pathological change in lung volume plus constricted or blocked airways.

In some embodiments, the subject in need of treatment has a lung remodeling disease that is associated with in a decrease in lung volume or a restriction in lung expansion. Non-limiting examples of lung remodeling diseases that decrease a subject's lung volume or restrict the expansion of the subject's lung include: asthma, chronic bronchitis, COPD, sarcoidosis, interstitial lungs diseases, e.g., hypersensitivity pneumonitis, collagen-vascular disease, eosinophilic granuloma, nonspecific interstitial pneumonitis, bronchiolitis obliterans with organizing pneumonia, respiratory bronchiolitis-associated interstitial lung disease, desquamative interstitial pneumonitis, lymphocytic interstitial pneumonitis, acute interstitial pneumonitis, bronchopulmonary dysplasia, restrictive lung disease; occupational lung diseases, e.g., asbestosis, bauxite fibrosis, beryliosis, byssinosis, coal worker's pneumoconiosis, hypersensitivity pneumonitis: including cork worker's lung, farmer's lung, pigeon breeder's lung, silo filler's disease and mushroom worker's lung; Labrador Lung disease, siderosis, silicosis and silicosiderosis; Caplan's syndrome, diseases associated with barotrauma and mechanical ventilation; high-altitude pulmonary edema, aspiration pneumonia, drug-induced pulmonary toxicity, lymphangioleiomyomatosis, lung transplantation rejection, e.g., bronchiolitis obliterans (BOS), pediatric and adult respiratory distress syndrome, acute respiratory distress syndrome, hyperoxia-induced bronchopulmonary dysplasia, and remodeling associated with pulmonary hypertension and pulmonary venoocclusive disease and cystic fibrosis.

In some embodiments, a lung remodeling disease that is associated with in a decrease in lung volume or a restriction in lung expansion is not idiopathic pulmonary fibrosis. In other embodiments, a lung remodeling disease that is associated with in a decrease in lung volume or a restriction in lung expansion is not bleomycin pulmonary toxicity.

In further embodiments, the drug associated with drug-induced pulmonary toxicity that results in a reduction of lung volume or lung function is selected from the list consisting of 5-fluorouracil (5FU), abacavir, abciximab, acebutolol, acetaminophen, acetazolamide, acetylcysteine, acetylsalicylic acid, acrylate, acyclovir, adalimumab, adenosine and derivatives, albumin, alemtuzumab, allopurinol, almitrine, alteplase, amifostine, aminoglutethimide, aminoglycosid antibiotics, aminorex, amiodarone, amitriptyline, amlodipine, amphotericin B, ampicillin, amrinone, anagrelide, anastrozole, angiotensin converting enzyme inhibitors, antazoline, anti TNF-alpha, non-steroidal anti-inflammatory drugs, anti-lymphocyte (thymocyte) globulin, anticoagulants, antidepressants, aprotinin, arsenic trioxide, atenolol, atociban, aurothiopropanosulfonate, azacitidine, azapropazone, azathioprine, azithromycin, balsazalide, barbiturates, basiliximab, BCG therapy, beclomethasone, benfluorex, benzbromarone, benzocaine, benzylthiouracil, bepridil, beta-agonists, beta-blockers, betahistine, betaxolol, bevacizumab, bicalutamide, blood transfusions, bortezomib, botulinum toxin, bromocriptine, bucillamine, bumetanide, buprenorphine, bupropion, busulfan, cabergoline, calcium salts, camptothecin, captopril, carbamazepine, carbimazole, carmustine (BCNU), carvedilol, cefotiam, celecoxib, celiprolol, cephalexin, cephalosporins, cetuximab, chlorambucil, chlorhexidine, chloroquine, chlorozotocin (DCNU), chlorpromazine, chlorpropamide, cilazapril, ciprofloxacin, cisapride, cisplatin, citalopram, cladribine, clarithromycin, clindamycin, clofazimine, clofibrate, clomiphene, clomipramine, clonidine, clopidogrel, clozapine, codeine, colchicine, contraceptives (oral), cotrimoxazole, cromoglycate, cyclophosphamide, cyclosporine, cyproterone acetate, cytarabine (cytosine arabinoside), cytokines, D-tubocurarine, danazol, dantrolene, dapsone, daptomycin, darbepoetin, dasatinib, daunorubicin, deferoxamine, desipramine, dexamethasone, dextran, diclofenac, diflunisal, dihydralazine, dihydro-5-azacytidine, dihydroergocristine, dihydroergocryptine, dihydroergotamine, diltiazem, dimethylsulphoxide, dipyridamole, disopyramide, divalproex sodium, docetaxel, dothiepin, doxorubicin, duloxetine, efavirenz, enalapril, epoprostenol, epinephrine, ergometrine, ergotamine, erlotinib, erythromycin, estrogens, etanercept, ethambutol, ethchlorvynol, ethosuximide, etoposide, etretinate, everolimus, Factor VIIa, famotidine, febarbamate, fenbufen, fenfluramine/dexfenfluramine, fenoprofen, fentanyl, fibrinolytics (including rTPA), flecainide, floxuridine, fliudarabine, fluoresceine, fluoxetine, flurbiprofen, flutamide, fluticasone, fluvastatin, folinic acid, fosinopril, fotemustine, furazolidone, G-CSF, GM-CSF, gefitinib (ZD1839), gemcitabine, gemtuzumab, glafenine, glibenclamide, gliclazide, gold salts, gonadotrophin, goserelin, haloperidol, heparin, heroin, hexamethonium, hydralazine, hydrochlorothiazide, hydrocortisone, hydroxyquinoleine, hydroxyurea, ibuprofen, ifenprodil, ifosfamide, imatinib, imidapril, imiglucerase, imipramine, immunoglobulins (IV), indinavir, indomethacin, infliximab, insulin, interferon alfa, interferon beta, interferon gamma, interleukin 2, iodine and iodinated radiographic contrast media, irinotecan, isoflurane, isoniazide, isotretinoin, itraconazole, ketamine, ketorolac, L-asparaginase, L-ryptophan, labetalol, lansoprazole, latanoprost leflunomide, lenalidomide, leukotrien receptor ntagonists, leuprorelin (leuprolide), levodopa, levofloxacin, levomepromazine, lidocaine, lipids, lisinopril, lisuride, lomustine (CCNU), losartan, loxoprofen, maprotiline, mazindol, mecamylamine, medroxyprogesterone, mefloquine, meloxicam, melphalan, mephenesin, mephenytoin, mercaptopurine, mesalamine (mesalazine, 5-ASA), mesulergine, metamizole (noramidopyrine), metapramine, metformine, methadone, methenolone, methimazole, methotrexate, methyldopa, methylphenidate, methylprednisolone, methysergide, metipranolol, metoclopramide, metoprolol, metronidazole, mexiletine, miconazole, midazolam minocycline, minoxidil, misoprostol, mitomycin C, mitoxantrone, montelukast, morphine, moxalactam, mycophenolate mofetil, nabumetone, nadolol, naftidrofuryl, nalbuphine, nalidixic acid, naloxone, naphtazoline, naproxen, nevirapine, nicardipine, nicergoline, niflumic acid, nilutamide, nimesulide, niridazol, nitric oxide, nitrofurantoin, nitroglycerin, nitrosoureas, nomifensine, OKT3, olsalazine, omalizumab, omeprazole, ornipressin, oxaliplatin, oxprenolol oxycodone, oxyphenbutazone, oxytocin, paclitaxel, pamidronate, para-(4)-aminosalicylic acid, paraffin (mineral oil), paraldehyde, parenteral nutrition, paroxetine, patent blue, pemetrexed, penicillamine, penicillins, pentamidine, pergolide, perindopril, phenazopyridine, phenylbutazone, phenylephrine, phenylpropanolamine, phenytoin (diphenylhydantoin), pindolol, pioglitazone, piperacilline, piroxicam, pituitary snuff, platinum salts, polyethylene glycol, practolol, pranlukast, pranoprofen, pravastatin, praziquantel, procainamide, procarbazine, progesterone, propafenone, propofol, propoxyphene/dextropropoxyphene, propranolol, propylene glycol, propylthiouracil, prostacyclin, prostaglandin E1, prostaglandin F2-alpha, protamine, pyrimethamine-dapsone, pyrimethamine-sulfadoxine, quinidine, quinine, raloxifene, raltitrexed, ranitidine, retinoic acid, rifampicin, riluzole, risedronate, risperidone, ritodrine, rituximab, rofecoxib, rosiglitazone, roxithromycin, salbutamol (Albuterol), serrapeptase, sertraline, sildenafil, simvastatin, sirolimus, sorafenib, sotalol, statins, steroids, streptokinase, streptomycin, sufentanil, sulfamides-sulfonamides, sulfasalazine (Salazopyrine), sulindac, sulprostone, tacrolimus (FK506), tamoxifen, telithromycin, telmisartan, temozolomide, temsirolimus, tenidap, terbutaline, tetracycline, thalidomide, thiazolidinediones, thiopental, tiaprofenic acid, ticlopidine, tiopronin, tirofiban, tizanidine, TNF-alpha, tocainide, tocilizumab, tolazamide, tolfenamic acid, topiramate, topotecan, tosufloxacin, tramadol, tranexamic acid, trastuzumab, trazodone, triazolam, trimipramine, triptans, trofosfamide, troglitazone, troleandomycin, trokinase, valproic acid, valsartan, vancomycin, vasopressin, venlafaxine, verteporfin, vinblastine, vindesine, vinorelbine, vitamin D, zafirlukast, zanamivir, zinostatin and zomepirac.

In some embodiments, the method for treating a lung remodeling disease that is associated with a decrease in lung volume or a restriction in lung expansion is capable of increasing the effective lung volume by at least 5%, 10%, 15%, 20%, 25%, 30%, 40%, 50%, 60% or 75% compared to a baseline measurement taken before treatment with an anti-CTGF agent. In further embodiments, the method for treating a lung remodeling disease associated with a decrease in lung volume or a restriction in lung expansion is capable of increasing a patient's $FEV_1$ or $FEV_6$ value by at least 5%, 10%, 15%, 20%, 25%, 30%, 40%, 50%, 60% or 75% compared to a baseline measurement of the patient's $FEV_1$ or $FEV_6$ before treatment with the anti-CTGF agent.

In other embodiments, the subject in need of treatment has a lung remodeling disease that results in an increase in lung volume (airspace enlargement). Non-limiting examples of lung remodeling diseases that feature an increase in a subject's lung volume include: emphysema, COPD; hyperoxia-induced bronchopulmonary dysplasia and remodeling associated with pulmonary hypertension and pulmonary venoocclusive disease. In some embodiments, the enlargement of the air spaces occurs across the entire respiratory acinus. In other embodiments, the enlargement of the air spaces occur from the respiratory bronchiole to the terminal bronchioles. In additional embodiments, the enlargement of the air spaces is associated with the destruction of the air space walls. In further embodiments, the enlargement of air spaces is associated with a reduction in lung elasticity.

In some embodiments, the method for treating a lung remodeling disease that is associated with an increase in lung volume is capable of decreasing the effective lung volume by at least 5%, 10%, 15%, 20%, 25%, 30%, 40%, 50%, 60% or 75% compared to a baseline measurement taken before treatment with an anti-CTGF agent. In further embodiments, the method for treating a lung remodeling disease that is associated with an increase in lung volume is capable of increasing a patient's $FEV_1$ or $FEV_6$ value by at least 5%, 10%, 15%, 20%, 25%, 30%, 40%, 50%, 60% or 75% compared to a baseline measurement of the patient's $FEV_1$ or $FEV_6$ before treatment with the anti-CTGF agent.

In further embodiments, the subject in need of treatment has a lung remodeling disease that is associated with constricted or blocked airways. Typically, constricted or blocked airways produce a shortness of breath. Frequently, a lung remodeling disease associated with constricted or blocked airways features excess mucus production that in severe cases occlude the small bronchi. Non-limiting examples of lung remodeling diseases associated with constricted or blocked airways include: asthma, COPD and chronic bronchitis. Typically, patients with a lung remodeling diseases associated with constricted or blocked airways have abnormally low $FEV_1$ or $FEV_6$ values. In some embodiments, the method for treating a lung remodeling diseases associated with constricted or blocked airways is capable of increasing a patient's $FEV_1$ or $FEV_6$ value by at least 5%, 10%, 15%, 20%, 25%, 30%, 40%, 50%, 60% or 75% compared to a baseline measurement of the patient's $FEV_1$ or $FEV_6$ before treatment with the anti-CTGF agent.

Frequently, lung remodeling diseases have an acute and/or chronic inflammatory phase. In many instances the lung inflammation is not associated with infection (pneumonitis). Usually, inflammation is associated with edema and an influx of immune cells such as mast cells, eosinophils, neutrophils and T lymphocytes. Typically, lung remodeling is associated with chronic inflammation that may affect different parts of the lung, including the walls of the bronchioles (bronchiolitis); the walls and air spaces of the alveoli (alveolitis); the small blood vessels (vasculitis). Remodeling associated with inflammation may include thickening of the lamina reticularis (the subepithelial reticular basement membrane surrounding airways), thickening of the airway wall, epithelial denudation, hypertrophy of the large bronchi, goblet cell hyperplasia, bronchial wall edema and narrowed small airways.

In some embodiments, the methods of the invention increase the elasticity of lung alveoli. In other embodiments, the methods of the invention prevent or reduce the incident of bullae formation. In other embodiments, the methods of the invention increase bulk air flow exchange. In further embodiments, the methods of the invention prevent, reduce or revert partial airway collapse. In additional embodiments, the methods of the invention prevent, reduce or revert, bronchial hypertrophy. In other embodiments, the methods of the invention preserve or increase alveoli density. In further embodiments, the methods of the invention prevent or reduce airway hyperresponsiveness (AHR). COPD and emphysema are lung remodeling diseases that are characterized by loss of alveolar elasticity and obstruction of bronchi and bronchioles. It has been shown that cigarette smoke, a known cause of these diseases, induces CTGF expression (Churg et al. (2006) *Am J Resp Crit Care Med* 174:1327-1334). The fact that early events in hyperoxia-induced neonatal lung disease resembles the lung remodeling that occurs in COPD and emphysema, as well as in other airway disease (asthma), suggest that anti-CTGF agents can be used effectively to treat lung remodeling diseases generally.

Anti-CTGF Agents

The methods of the invention are accomplished by administering to a subject an anti-CTGF agent. As used herein, the term "anti-CTGF agent" refers to any agent, molecule, macromolecule, compound, or composition that inhibits, reduces, or stops the activity, function, production or expression of connective tissue growth factor. Anti-CTGF agents include antibodies, antibody fragments, antibody mimetics, antisense oligonucleotides, siRNA, miRNA, ribozymes, aptamers and small molecules. The anti-CTGF agent is preferably one that is specific for CTGF and exerts its effect directly and specifically on the CTGF protein or on the CTGF gene or mRNA, rather than a non-specific inhibitor (e.g., a non-specific protease or transcription inhibitor) or an indirect inhibitor (e.g., an inhibitor of an upstream or downstream signaling pathway). As used herein, "connective tissue growth factor" and "CTGF" refer to a matricellular protein belonging to a family of proteins identified as CCN proteins. CTGF may also be referred to within the art as "hypertrophic chondrocyte-specific protein 24," "insulin-like growth factor-binding protein," and "CCN2."

In some embodiments, an antibody that binds specifically to CTGF may be used in the present methods. In some embodiments, the antibody for use in the present methods is obtained from the same species as the subject in need. In other embodiments, the antibody is a chimeric antibody wherein the constant domains are obtained from the same species as the subject in need and the variable domains are obtained from another species. For example, in treating a human subject the antibody for use in the present methods may be a chimeric antibody having constant domains that are human in origin and variable domains that are mouse in origin. In preferred embodiments, the antibody for use in the present methods binds specifically to the CTGF endogenous to the species of the subject in need. Thus, in certain embodiments, the antibody is a human or humanized antibody, particularly a monoclonal antibody, that specifically binds human CTGF (GenBank Accession No. NP_001892.1). In particular embodiments, the antibody is the antibody described and claimed in U.S. Pat. No. 7,871,617. In some embodiments, the antibody has the amino acid sequence of the antibody produced by the cell line identified by ATCC Accession No. PTA-6006. In other embodiments, the antibody competitively binds to CTGF with an antibody produced by ATCC Accession No. PTA-6006. A particular antibody for use in the present methods is CLN1 or mAb1 as described in U.S. Pat. No. 7,405,274, or an antibody substantially equivalent thereto or derived therefrom. An antibody for use in the present methods may also be a fragment such as a Fab, F(ab)2, Fv, or single chain variable fragment (scFV) of any antibody described above. An antibody for use in the present methods may also be derived from any antibody described above. Such derivatives may include any suitable antibody derivation known to those of skill in the art and include, but are not limited to, diabodies, triabodies, and minibodies.

Antibody CLN1 is produced by the cell line defined by ATCC Accession No. PTA-6006, deposited with the American Type Culture Collection (ATCC, 10801 University Boulevard, Manassas, Va. 20110-2209) on 20 May 2004.

Additionally, antibodies for use in the present methods also include antibody mimetics. Antibody mimetics are proteins, typically in the range of 3-25 kD that are designed to bind an antigen with high specificity and affinity like an antibody, but are structurally unrelated to antibodies. Frequently, antibody mimetics are based on a structural motif or scaffold that can be found as a single or repeated domain from a larger biomolecule. Examples of domain derived antibody mimetics included AdNectins that utilize the 10th fibronectin III domain (Lipovšek D. *Protein Eng Des Sel,* 2010, 24:3-9); Affibodies that utilize the Z domain of staphylococcal protein A (Nord K et al. *Nat Biotechnol.* 1997, 15: 772-777) and DARPins that utilize the consensus ankyrin repeat domain (Amstutz P. *Protein Eng Des Sel.* 2006, 19:219-229. Alternatively, antibody mimetics can also be based on the entire structure of a smaller biomolecule, such as Anticalins that utilize the lipocalin structure (Beste G et al. *Proc Natl Acad Sci USA.* 1999, 5:1898-1903)

As referred to herein, the phrase "an antibody that specifically binds to CTGF" includes any antibody that binds to CTGF with high affinity. Affinity can be calculated from the following equation:

$$\text{Affinity} = K_a = \frac{[Ab \cdot Ag]}{[Ab][Ag]} = \frac{1}{K_d}$$

where [Ab] is the concentration of the free antigen binding site on the antibody, [Ag] is the concentration of the free antigen, [Ab·Ag] is the concentration of occupied antigen binding sites, $K_a$ is the association constant of the complex of antigen with antigen binding site, and $K_d$ is the dissociation constant of the complex.

A high-affinity antibody typically has an affinity at least on the order of $10^8$ $M^{-1}$, $10^9$ $M^{-1}$ or $10^{10}$ $M^{-1}$. In particular embodiments, an antibody for use in the present methods will have a binding affinity for CTGF between of $10^8$ $M^{-1}$ and $10^{10}$ $M^{-1}$, between $10^8$ $M^{-1}$ and $10^9$ $M^{-1}$ or between $10^9$ $M^{-1}$ and $10^{10}$ $M^{-1}$. In some embodiments the high-affinity antibody has an affinity of about $10^8$ $M^{-1}$, $10^9$ $M^{-1}$ or $10^{10}$ $M^{-1}$.

In some embodiments, polynucleotide inhibitors of CTGF, including small interfering ribonucleic acids (siR-NAs), micro-RNAs (miRNAs), and antisense sequences may be used in the present methods to inhibit expression and/or production of CTGF. (See, e.g., Kondo et al. (2000) Biochem Biophys Res Commun 278:119-124.) Such techniques are well-known to those of skill in the relevant art. Polynucleotide inhibitors that target CTGF expression have been described and utilized to reduce CTGF expression in various cell types. (See, e.g., International Publication No. WO 96/38172; International Publication No. WO 00/27868; international Publication No. WO 00/35936; International Publication No. WO 03/053340; Kothapalli et al. (1997) Cell Growth Differ 8:61-68; Shimo et al. (1998) J Biochem (Tokyo) 124:130-140; Uchio et al. (2004) Wound Repair Regen 12:60-66; Guha et al. (2007) FASEB J 21:3355-3368; U.S. Pat. No. 6,358,741; U.S. Pat. No. 6,965,025; U.S. Pat. No. 7,462,602; U.S. Patent Application Publication No. 2008/0070856; U.S. Patent Application Publication No. 2008/0176964.) CTGF antisense constructs and other types of polynucleotide inhibitors of CTGF can be used to reduce expression of CTGF and thereby treat lung remodeling disease. Such constructs can be designed using appropriate vectors and expressional regulators for cell- or tissue-specific expression and constitutive or inducible expression. Such genetic constructs can be formulated and administered according to established procedures within the art. The polynucleotide inhibitors used in the present methods and medicaments may be made using solid phase synthesis techniques known to those of skill in the art and available through various vendors including GE Healthcare Biosciences (Piscataway, N.J.). Any other means for such synthesis known in the art may additionally or alternatively be employed.

Pharmaceutical Formulations and Routes of Administration

The anti-CTGF agents used in the methods of the present invention can be delivered directly or in pharmaceutical compositions containing excipients, as is well known in the art. An effective amount of anti-CTGF agent can readily be determined by routine experimentation, as can an effective and convenient mute of administration and an appropriate formulation. Various formulations and drug delivery systems are available in the art. (See, e.g., Gennaro, ed. (2000) Remington's Pharmaceutical Sciences, supra; and Goodman and Gilman's The Pharmacological Basis of Therapeutics, 10$^{th}$ Ed. (2001), Hardman, Limbird, and Gilman, eds. MacGraw Hill Intl.) Typically, the anti-CTGF agent is administered in an amount sufficient to provide therapeutic efficacy over the treatment time course. Therapeutic efficacy can be measured using any parameter provided herein, including improvement in any pathological feature of lung remodeling disease and/or improvement in lung function.

Therefore, in one embodiment, the present invention provides methods for treatment of lung remodeling disease in a subject, wherein the method comprises administering to the subject an anti-CTGF agent. In another embodiment, the present invention provides methods for pre-treating a subject at increased probability of being afflicted with lung remodeling disease, wherein the method comprises administering to the subject an anti-CTGF agent. The methods of the present invention prevent, reduce, stabilize, normalize or reverse various pathological features of lung remodeling disease. Such features include, but are not limited to, decreased lung volume, increased lung density, remodeled lung tissue, and increased mortality. Thus, in one embodiment, the present methods provide a method of reducing, stabilizing or normalizing a pathological feature associated with lung remodeling disease in a subject, the method comprising administering to the subject an anti-CTGF agent, thereby reducing, stabilizing or normalizing the pathological feature of lung remodeling disease. Stabilizing of pathological features is defined as reducing, slowing or freezing the rate of decline of a pathological change in a lung tissue or in a lung parameter. In some embodiments, stabilization is the reduction in the rate at which a particular lung function is loss. In certain embodiments, stabilization reduces the rate of a pathological change in a particular lung function by at least 5%, 10%, 15%, 20%, 25%, 30%, 35%, 40%, 45%, 50%, 75% or 100% compared to the expected rate of change based on a control population or a historical population. In other embodiments, stabilization results in a halting of the rate of change in a particular lung function by the pathologic process thereby halting the deterioration in the patient's lung function.

In other embodiments, normalization is the return to a normal range of a characteristic of a lung tissue or lung function. In some embodiments, normalization results in the characteristic of the lung tissue or lung parameter being within the normal range or less than 5%, 10%, 15% or 20% away from the normal range. For instance, a patient with a lung remodeling disease that had an initial lung density of −300 HU that increased to a lung density within the normal range of −800 to −900 HU after therapy with an anti-CTGF agent would be classified as having normalized lung density. Similarly, a patient with a lung remodeling disease that had an initial PaO$_2$ of 68% that increased to a PaO$_2$ of 81% after treatment with an anti-CTGF agent would be classified as having a normalized PaO$_2$ as a value of 80% or above is within the normal range, see infra.

In another embodiment, the present invention provides a method for pre-treating a subject at increased probability of being afflicted with lung remodeling disease to prevent or reduce a resulting pathological feature of lung remodeling disease, the method comprising administering to the subject an anti-CTGF agent, thereby preventing or reducing a resulting pathological feature of lung remodeling disease. In various embodiments, the pathological feature of lung remodeling disease is selected from the group consisting of decreased lung volume, increased lung density, remodeled lung tissue, and increased mortality.

In one embodiment, the present invention provides a method of normalizing or stabilizing lung density in a subject having lung remodeling disease, the method comprising administering to the subject an anti-CTGF agent, thereby normalizing or stabilizing lung density in the subject. In another embodiment, the present invention provides methods of preventing or reducing a pathological change in lung density in a subject at increased probability of being afflicted with lung remodeling disease, the method comprising administering to the subject an anti-CTGF agent, thereby preventing or reducing the pathological change in lung density in the subject. Lung density may be measured by any method known to one of skill in the art. In one particular aspect, the lung density is measured by computed tomography (CT) scan; more particularly, lung density is measured by high resolution CT (HRCT). In particular embodiments, lung density is measured in Hounsfield Units (HU), and improvement in lung density as a result of the present methods is measured as a decrease in measured HU. On the Hounsfield scale, lung zones with a density between −900 and −800 HU are typically considered within a normal aerated range, while those between −500 and −100 are poorly aerated and those between −100 and +100 are nonaerated. In some embodiments, the subject having increased lung density has a lung density of greater than −800 HU, greater than −700 HU, greater than −600 HU, greater than −500 HU, greater than −400 HU, or greater than −300 HU. In some embodiments, the subject having increased lung density has a lung density between −700 and +100 HU, between −600 and +100 HU, between −500 and +100 HU, between −500 and −100 HU, between −700 and +100 HU or between −500 and −300 HU. In some embodiments, the subject having decreased lung density has a lung density of less than −800 HU, less than −900 HU, less than −910 HU, less than −950 HU. In some embodiments, treatment with an anti-CTGF agent changes the lung density of the patient by at least 100 HU, at least 150 HU, at least 200 HU, at least 250 HU or at least 300 HU towards the normal range HU range of −800 to −900 HU. In other embodiments, treatment with an anti-CTGF agent normalizes the patient's lung density, i.e., changes the lung density so that after treatment the lung density is within the normal range of −800 to −900 HU. Improvement in lung density may additionally be measured by or associated with improved lung function as described infra.

In another embodiment, the present invention provides a method of reducing or stabilizing lung remodeling in a subject having lung remodeling disease, the method comprising administering to the subject an anti-CTGF agent, thereby reducing or stabilizing lung remodeling in the subject. In another embodiment, the present invention provides a method of preventing or reducing lung remodeling in a subject at increased probability of being afflicted with lung remodeling disease, the method comprising administering to the subject an anti-CTGF agent, thereby preventing or reducing lung remodeling in the subject. Lung remodeling may be measured by any method known to one of skill in the art. In some embodiments, lung remodeling is measured using lung images from CT scan; more particularly, by HRCT. In other embodiments, lung remodeling is measured by lung biopsy and histology. In subjects having lung remodeling disease, portions of normal lung may be replaced by fibrotic septae between dilated airspaces, the gross appearance being referred to as 'honeycomb changes.' Lung remodeling in lung remodeling disease generally shows patchy, heterogeneous regions of dense fibrosis and mild or moderate interstitial lymphoplamacytic infiltrates, architectural remodeling, honeycomb change, and fibroblastic foci. Fibroblastic foci represent zones of disease activity whose extensiveness has been linked to survival. In some embodiments, lung remodeling is measured as a change in potential airspace, i.e., the fraction of lung not occupied by tissue as assessed, e.g., by histology of biopsy material. In particular embodiments, the present methods are used to treat a subject having decreased potential airspace relative to normal. In other embodiments, lung remodeling is measured by percentage of lung showing honeycomb changes or fibroblastic foci. In particular embodiments, the present methods are used to treat a subject having increased percentage of honeycomb change or increased number of fibroblastic foci. Lung remodeling diseases are frequently associated with airway smooth muscle hypertrophy allowing for measurement of lung remodeling based on the extent of hypertrophy. Lung remodeling may additionally be measured by or associated with decreased lung function as described infra.

Subjects having lung remodeling disease are at high risk of acute or chronic respiratory failure and cardiovascular complications which lead to increased mortality. Thus, in yet another embodiment, the present invention provides a method of increasing the likelihood of survival in a subject having lung remodeling disease, the method comprising administering to the subject an anti-CTGF agent, thereby increasing the likelihood of survival in the subject. Increased likelihood of survival may also be associated with improved lung function as described infra. In further embodiments, the methods of the invention improve the survival of subjects treated with an anti-CTGF agent by at least 5%, 10%, 15%, 20%, 25%, 30%, 35%, 40%, 50%, 60%, 65%, 70%, 75%, 80%, 90%, 100%, 125%, 150% or 200% compared to a control group that is not treated with an anti-CTGF agent.

In various embodiments, the methods of the invention improve lung function. Improved lung function may be determined by any measure known to those of skill in the art. In some embodiments, lung function is determined by measuring blood gas parameters, e.g., partial arterial pressure of oxygen ($PaO_2$) or percent oxygen saturation of blood. For instance, improvement in lung function can be demonstrated in subjects having low $PaO_2$ by measuring the ability of the present methods to increase $PaO_2$. Typically, values for $PaO_2$ greater than 80 mmHg are considered normal, whereas values of 80 mmHg or less indicate a state of hypoxia or hypoxemia. Although oxygen saturation ($O_2$ Sat) usually correlates with $PaO_2$, the relationship is not linear. For non-shifted $O_2$ Sat, a value of 100% corresponds to 90 mmHg $PaO_2$, a value of 90% corresponds to 60 mmHg, and a value of 60% corresponds to 30 mmHg. Factors that can cause a shift in the correlative values include temperature and pH. In various embodiments, the present methods are used to treat a subject having a $PaO_2$ of below 80 mmHg, particularly below 75 mmHg, and more particularly below 70 mmHg. In particular embodiments, blood gas parameters are normalized over the treatment time course. In some embodiments, treatment with an anti-CTGF agent results in an increase in a subject's $PaO_2$ value of at least 1%, 2%, 3%, 4%, 5%, 6%, 7%, 8%, 9%, 10%, 15%, 20%, 25% or 30% above an initial baseline value obtained prior to the initiation of treatment.

In some embodiments, lung function is determined by measuring lung volume parameters or lung function parameters, e.g., vital capacity, residual volume (RV), forced expiratory volume (FEV), forced vital capacity (FVC), forced expiratory flow (FEF), tidal volume (TV), maximum flow (Vmax), peak expiratory flow rate (PEFR), inspiratory reserve volume (IRV), functional residual capacity (FRC), total lung capacity (TLC), expiratory reserve volume (ERV) and/or maximum voluntary ventilation (MVV). Total lung volume or total lung capacity refers to the volume in the lungs upon maximal inspiration, and in a normal adult is 4-6 L. Tables 1 and 2 provide various measured and derived lung volumes. The vital capacity and force vital capacity is the maximal volume expelled from the lungs after maximal inspiration and is typically about 4.8 L for men and about 3.2 L for women. Residual volume refers to the volume remaining in the lungs after maximal expiration, and in a normal adult is about 1.0-1.2 L. FEV measures the volume of air exhaled over a pre-determined period of time by a forced expiration immediately after a full inspiration, typically over 1 second ($FEV_1$) or six seconds ($FEV_6$). Vmax is the maximum flow measured during FVC. PEFR measures the maximum flow rate during a forced exhale starting from full inspiration.

The various lung volume measurements and other lung function parameters can be readily measured through the use of a spirometer as is well known in the art. Lung volume measurements and other lung function parameters depend on the gender, age, ethnicity and height of the subject, but spirometric reference values are widely known and available in the art. (See Hankinson et al. Am J Respir Crit Care Med. 1999; 159(1):179-187) Further, computer programs are readily available for the calculation of spirometry reference values based on a patient's specific gender, ethnicity, age and height. (See Centers for Disease Control and Prevention website)

TABLE 1

Average lung volumes in healthy adults

| Volume | Value (liters) | |
|---|---|---|
| | In men | In women |
| Inspiratory reserve volume | 3.3 | 1.9 |
| Tidal volume | 0.5 | 0.5 |
| Expiratory reserve volume | 1.0 | 0.7 |
| Residual volume | 1.2 | 1.1 |

Ganong, W. *Review of Medical Physiology* (21st ed.)

TABLE 2

Lung capacities in healthy adults

| Volume | Average value (liters) | | Derivation |
|---|---|---|---|
| | In men | In women | |
| Vital capacity | 4.8 | 3.1 | IRV plus TV plus ERV |
| Inspiratory capacity | 3.8 | 2.4 | IRV plus TV |
| Functional residual capacity | 2.2 | 1.8 | ERV plus RV |
| Total lung capacity | 6.0 | 4.2 | IRV plus TV plus ERV plus RV |

Ganong, W. *Review of Medical Physiology* (21st ed.)

In some embodiments, the present methods improve lung function in a subject having reduced lung function associated with a lung remodeling disease as determined by measuring one or more lung volume parameters. In certain embodiments, the subject has below inspiratory reserve volume, expiratory reserve volume, vital capacity and/or total lung capacity and the methods of the invention increase one or more of these lung volume parameters. In particular embodiments, one or more lung volume parameters are normalized over the treatment time course.

In some embodiments, the methods of the invention will increase at least one lung volume parameter of a patient suffering for a lung remodeling disease associated with in a decrease in a lung volume parameter or a restriction in lung expansion. In certain embodiments, the increase in the at least one lung volume parameter is an at least 5%, 10%, 115%, 20%, 25%, 30%, 35%, 40% or 50% increase compared to a baseline measurement taken before treatment.

In some embodiments, lung function is determined by measuring the cell number and cellular make-up of bronchoalveolar lavage (BAL) fluid and/or sputum. Table 3 provides normal sputum cell count values. (See Brightling C E. *Chest.* 2006: 129(5):1344-1348) The total cell count gives a measure of the intensity of any inflammation and the differential of the type. At early stages of lung remodeling disease, the alveolar and adjacent capillary endothelial cells become leaky, leading to alveolar and interstitial edema that is accompanied by an increase in the number of immune cells found in BAL fluid and/or sputum. In particular, the number of polymorphonuclear leukocytes (PMNs), which normally comprise about 1-3% of the cellular component of BAL or sputum, can increase to 20% or more. Therefore, in various embodiments, the present methods are used to treat a subject having an elevated percentage of PMNs in BAL fluid and/or sputum and the methods of the invention reduce the percentage of PMNs in BAL fluid and/or sputum. In particular embodiments, the present methods are used to treat a subject having greater than 5% PMNs in BAL fluid and/or sputum, particularly greater than 10%, and more particularly greater than 15%. In particular embodiments, the cellular make-up of BAL fluid and/or sputum is normalized over the treatment time course. Sputum sample can be spontaneously obtained or induced with an aerosol of normal or hypertonic saline. Treatment of a lung remodeling disease with an anti-CTGF agent can be monitored through analysis of BAL fluid and/or sputum and the dose adjusted to reduce the total cell count and also to change the percent composition of the BAL fluid and/or sputum.

TABLE 3

Normal Sputum Cell Count Values

| Sputum Cell Count | Mean | Mean + 2 SD | Median | 90th Percentile |
|---|---|---|---|---|
| Total cells, $10^6$/g | 4.1 | 13.8 | 2.4 | 9.7 |
| Eosinophils, % | 0.4 | 2.2 | 0.0 | 1.1 |
| Neutrophils, % | 37.5 | 77.7 | 36.7 | 64.4 |
| Macrophages, % | 58.8 | 100 | 60.8 | 86.1 |
| Lymphocytes, % | 1.0 | 3.2 | 0.5 | 2.6 |
| Metachromatic, % | 0.0 | 0.1 | 0.0 | 0.04 |

In various embodiments, the method may be applied at appropriate intervals to achieve the claimed result, such as improved lung function as measured by any of the parameters provided herein. In particular embodiments, the methods may be applied 1, 2, 3, 4, or 5 time per month. In some embodiments, the methods are applied 1 time per week or 1 time every other week. In various embodiments, the methods are continued until the pathological feature or functional parameter is essentially normalized or the subject is no longer considered at risk. The anti-CTGF agent can be administered by any conventional route with systemic and pulmonary administration preferred.

In various embodiments, the anti-CTGF agent may be administered at appropriate levels to achieve the desired pharmacological effect. In particular embodiments, the anti-CTGF agent is an antibody that binds specifically to CTGF. In various embodiments, the antibody may be administered at a dose of from 0.01 to 100 mg of antibody/kg of patient weight, more particularly from 0.1 to 50 mg/kg, and even more particularly from 1-30 mg/kg. Doses particularly contemplated for use in the present methods include, but are not limited to, at least 3 mg/kg, 5 mg/kg, 10 mg/kg, 15 mg/kg 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg or 100 mg/kg. Depending on the type and severity of the disease, about 0.01 to 100 mg/kg is an initial candidate dosage for administration to the patient, whether, for example, by one or more separate administrations, or by continuous infusion. For repeated administrations over several days or longer, depending on the condition, the treatment is repeated until a desired suppression or reversal of disease symptoms occurs. In some embodiments, an initial higher antibody induction or loading dose is first used to suppress or reverse a disease symptom and then the patient is treated with a lower antibody maintenance dose. Other dosage regimens may be useful and are not excluded from the present invention.

In various embodiments, the anti-CTGF agent may be administered by any route that provides a suitable pharmacokinetic profile. In particular embodiments, the anti-CTGF agent is administered intravenously. In further embodiments, the anti-CTGF agent is administered intravenously in a single bolus injection. In other embodiments, the anti-CTGF agent is administered intravenously by infusion. In additional embodiments, the anti-CTGF agent is administered as particulate or aerosol directly to the lungs. In other embodiments, the anti-CTGF agent may be administered subcutaneously, intramuscularly, or intraperitoneally.

The methods of the present invention, as exemplified herein, clearly demonstrate that the administration of an anti-CTGF agent significantly improves lung density, lung function, and survival at all treatment periods. Thus, administration of an anti-CTGF agent provides significant benefit to a subject whether the anti-CTGF agent is administered prior to an initial insult or at any time subsequent to the initial insult. The data also clearly demonstrates that administration of an anti-CTGF agent does benefit a patient already in a chronic progressive phase of a lung remodeling disease. Therefore, in some embodiments, the anti-CTGF agent is administered at or near the time of initial diagnosis of a lung remodeling disease. In other embodiments, the anti-CTGF agent may be initiated prior to an event associated with increased probability or likelihood of being afflicted with lung remodeling disease. Such an event may be an occupational event, e.g., potential exposure to an agent known or suspected of causing lung remodeling disease. For example, the anti-CTGF agent may be used to pre-treat a worker that may be exposed to asbestos as part of an asbestos abatement project. Such an event may be a medical event, e.g., exposure to a medical therapy or procedure known or suspected of causing a lung remodeling disease. For example, the anti-CTGF agent may be used to pre-treat a patient that is going to be exposed to ionizing radiation as part of radiation therapy.

In another aspect, the present invention provides medicaments for treatment of lung remodeling disease. In one embodiment, the present invention provides the use of an anti-CTGF agent in preparing a medicament for treating lung remodeling disease. The medicament may be used to prevent, reduce, reverse, normalize, and/or stabilize various pathological features of lung remodeling disease. Such features include, but are not limited to, decreased lung volume, increased lung density, the presence of remodeled lung tissue, and increased probability of mortality. In another embodiment, the present invention provides the use of an anti-CTGF agent in preparing a medicament for preventing or reducing a pulmonary disorder in a subject at increased probability of being afflicted with a lung remodeling disease. In various embodiments, the medicament also improves lung function in a subject having lung remodeling disease.

Any anti-CTGF agent that directly inhibits the expression or activity of CTGF may be used in formulating the present medicaments. In particular embodiments, the anti-CTGF agent is an antibody that binds specifically to CTGF, or a polynucleotide inhibitor of CTGF expression (for example, an antisense oligonucleotide, siRNA, shRNA, or miRNA). In a preferred embodiment, the anti-CTGF agent is an antibody that binds specifically to CTGF. Any antibody that specifically binds to CTGF may be used in formulating the present medicaments. Antibodies for use in the present medicaments are described supra. In various embodiments, the antibody for use in the present medicaments is an antibody described and claimed in U.S. Pat. No. 7,871,617. In particular embodiments, the antibody has the amino acid sequence of the antibody produced by the cell line identified by ATCC Accession No. PTA-6006. In other embodiments, the antibody competitively binds to CTGF with an antibody produced by ATCC Accession No. PTA-6006. A particular antibody for use in the present medicaments is CLN1 or mAb1 as described in U.S. Pat. No. 7,405,274, or an antibody substantially equivalent thereto or derived therefrom.

The medicament may be formulated for the intended route of administration. Such formulations may encompass pharmaceutically acceptable carriers that are inherently nontoxic and nontherapeutic. Polynucleotide inhibitors may be admixed, encapsulated, conjugated or otherwise associated with other molecules, molecule structures or mixtures of compounds, e.g., liposomes, receptor targeted molecules, oral, rectal, topical, systemic, aerosolized, nebulized or other formulations, for assisting in uptake, distribution and/or absorption. (See, e.g., U.S. Pat. No. 5,108,921; U.S. Pat. No. 5,354,844; U.S. Pat. No. 5,416,016; U.S. Pat. No. 5,459,127; U.S. Pat. No. 5,521,291; U.S. Pat. No. 5,543,158; U.S. Pat. No. 5,547,932; U.S. Pat. No. 5,583,020; U.S. Pat. No. 5,591,721; U.S. Pat. No. 4,426,330; U.S. Pat. No. 4,534,899; U.S. Pat. No. 5,013,556; U.S. Pat. No. 5,108,921; U.S. Pat. No. 5,213,804; U.S. Pat. No. 5,227,170; U.S. Pat. No. 5,264,221; U.S. Pat. No. 5,356,633; U.S. Pat. No. 5,395,619; U.S. Pat. No. 5,416,016; U.S. Pat. No. 5,417,978; U.S. Pat. No. 5,462,854; U.S. Pat. No. 5,469,854; U.S. Pat. No. 5,512,295; U.S. Pat. No. 5,527,528; U.S. Pat. No. 5,534,259; U.S. Pat. No. 5,543,152; U.S. Pat. No. 5,556,948; U.S. Pat. No. 5,580,575; and U.S. Pat. No. 5,595,756.)

Examples of carriers for use with antibodies include ion exchangers, alumina, aluminum stearate, lecithin; serum proteins such as human serum albumin; buffers such as phosphate, histidine, or glycine; sorbic acid, potassium sorbate, partial glyceride mixtures of saturated vegetable fatty acids, water, salts; or electrolytes such as protamine sulfate, sodium chloride, metal salts, colloidal silica, magnesium trisilicate, polyvinyl pyrrolidone, cellulosic polymers, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms include, for example, microcapsules, nano-capsules, liposomes, plasters, sublingual tablets, and polymer matrices such as polylactide:polyglycolide copolymers. When present in an aqueous dosage form, rather than being lyophilized, the antibody typically will be formulated at a concentration of about 0.1 mg/ml to 100 mg/ml, although wide variation outside of these ranges is permitted.

The present invention contemplates the use of the present methods in combination with other therapies. In one embodiment, the method is used in combination with another therapy, e.g., to further augment therapeutic effect on certain pathological events, etc. The two treatments may be administered at the same time or consecutively, e.g., during a treatment time course or following disease progression and remission. In another embodiment, the method is used in combination with another therapeutic method having a similar or different mode of action, e.g., a corticosteroid. Current therapeutic approaches to treat lung remodeling are known by one of skill in the art, and include, for example, corticosteroids, bronchodilators, anticholinergics, vasodilators, diuretics, anti-hypertensive agents, acetazolamide, antibiotics, immunosuppressive drugs, surfactants, supplemental oxygen and mechanical ventilation. Use of any of these therapeutic agents in combination with the use of methods of the present invention is specifically contemplated.

The medicaments may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising an agent of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

The invention will be further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Radiation Induced Lung Remodeling

Materials and Methods
Experimental Protocol and Animal Model

Female C57BL/6 mice (8-wk-old; approximate body weight: 20 g; Charles River Laboratories) were randomized into 8 groups of 25 animals and were supplied with food and water ad libitum. Six groups (150 mice) were irradiated (IR) with a single dose of 20 Gy at day 0. Mice were anesthetized by intraperitoneal application of 0.2 mg/kg Rompun (Bayer) and 100 mg/kg ketamin 10% (Parke-Davis). Photon irradiation was administered as a single 20 Gy dose to the entire thorax (Siemens linear accelerator, source surface distance of 1 m; irradiation field of 0.02×0.2 m). Other organs, above and below the thorax, were shielded.

The anti-CTGF monoclonal antibody (CLN1) used in this experiment is described and claimed in U.S. Pat. No. 7,405,274. Irradiated mice were administered either no therapeutic (25 mice), control IgG (25 mice), or CLN1 (100 mice). Animals receiving CLN1 were randomized into groups to receive antibody therapy beginning either 2 days before (25 mice; d−2), 2 days after (25 mice; d+2), 20 days after (25 mice; d+20), or 112 days after (25 mice; d+112) irradiation. In each CLN1 group, antibody was administered at a dose of 10 mg/kg by intraperitoneal (i.p.) injection three times per week for a dosing period of 8 weeks. The two unirradiated groups received either control IgG or CLN1 for the first 8 weeks of the experiment. A schematic of the different dosing schedules is provided in FIG. 1A.

Lung Imaging

To obtain independent qualitative and quantitative measures for lung remodeling in the mice, high resolution computed tomography (HRCT) was performed in every surviving mouse from each group on weeks 4, 8, 12, 16, 18, 20, 22, 24, 30 and 48 after irradiation. CT images were captured on a SOMATOM PLUS 4 VOLUME ZOOM multi-slice CT scanner (Siemens). 120 kV with 100 mAS were applied. 0.5-mm thin slices with 0.5-mm inter-slice distance spanned the complete mouse chest (a total acquisition time of 0.5 s). Multiplanar reconstructions were performed for semiquantitative analysis. The Hounsfield units (HU) of section slices from the upper, middle and lower lung regions were determined. Density on CT is often described by Hounsefield Units, where pure water measures 0 HU, air measures −1,000 HU, and very dense structures such as bone approach +1,000 HU. After an initial examination of the whole lung, representative slides were chosen to undergo further analysis. Three slides of the lung, representing the upper (5 slides below the apex), middle (divorce of the trachea) and lower (about 5 slides above the diaphragmatic dome) region were selected and measured quantitatively by Hounsfield Units. Six circles were set in the selected fields of both sides of the lung, representing the upper anterior and posterior, the middle anterior and posterior and the lower anterior and posterior region, thus collecting twelve sets of data per mouse. Circles were set as large as possible, but avoiding big bronchi and vessels. All examinations were performed with the same window and level settings (400/1000). Total arithmetic means±standard error of the mean (SEM) of the HU were calculated.

Lung Histology

Histological analysis from mice tissues was performed as described in Plathow et al. (2004) *Invest. Radiol.* 39:600-609. In brief, lungs were fixed by intratracheal instillation of 4% formalin followed by overnight fixation, embedded in paraffin, sectioned at 5 µm, and stained with hematoxylin and eosin (H&E), Sirius red or Masson's trichrome. The total count of leukocytes, and septal thickness were determined by morphometric evaluation (Q 600 Quantimet; Leica).

Statistics

Mouse survival curves after thoracic irradiation and CLN1 treatments were calculated with the Kaplan-Meier method and compared using the log-rank test. Other quantitative data are given as mean values±SEM or as indicated. For analysis of differences between the groups, ANOVA followed by the appropriate post hoc test for individual comparisons between the groups was performed. All tests were two-tailed. P<0.05 was considered statistically significant.

Results
Course of Radiation-Induced Lung Damage

Figure 1B:
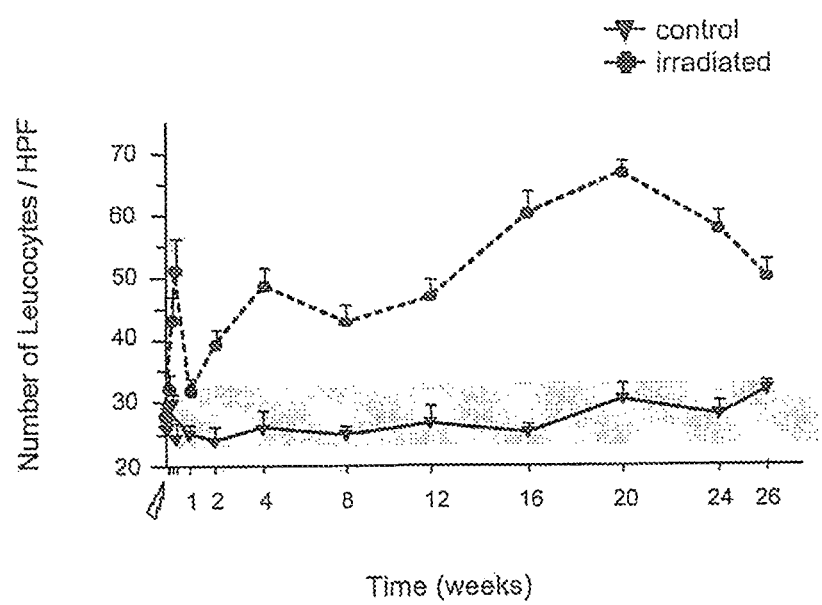
Figure 1C:
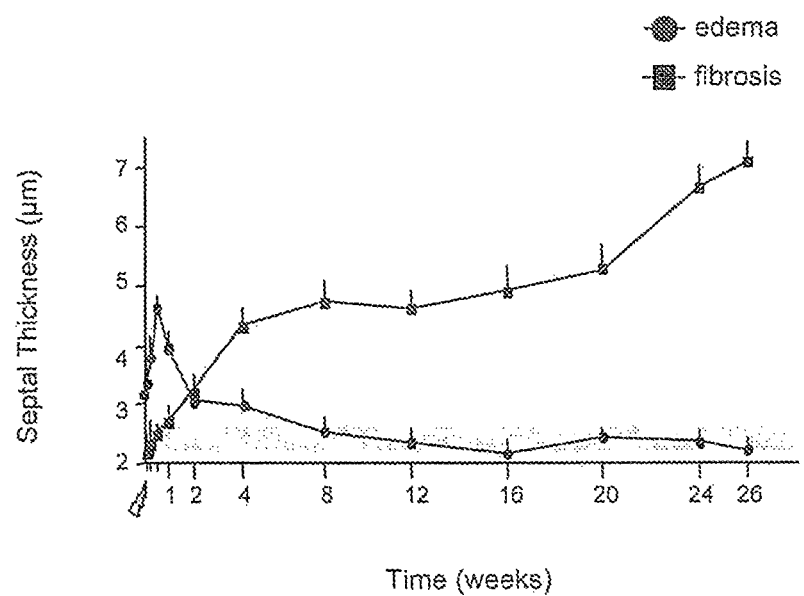

The present model of radiation-induced pulmonary disorders utilizes a single dose of ionizing radiation as an initial insult. Exposure of normal lung tissue to irradiation produces an acute pneumonitis and a progressive, long-term fibrosis (see, e.g., Movsas et al. (1997) *Chest* 111:1061-1076). Characteristic histologic findings in the pneumonitis phase of the radiation response include prominent inflammatory cell infiltrates in the alveoli and lung interstitium with simultaneous interstitial edema. Both parameters typically exhibit similar kinetics in the acute phase, reaching their maximum about 72 h after radiation injury. After the acute radiation response, both leukocyte count and septal edema spontaneously subside within a few days. (See FIGS. 1B and 1C.)

Figure 1D:
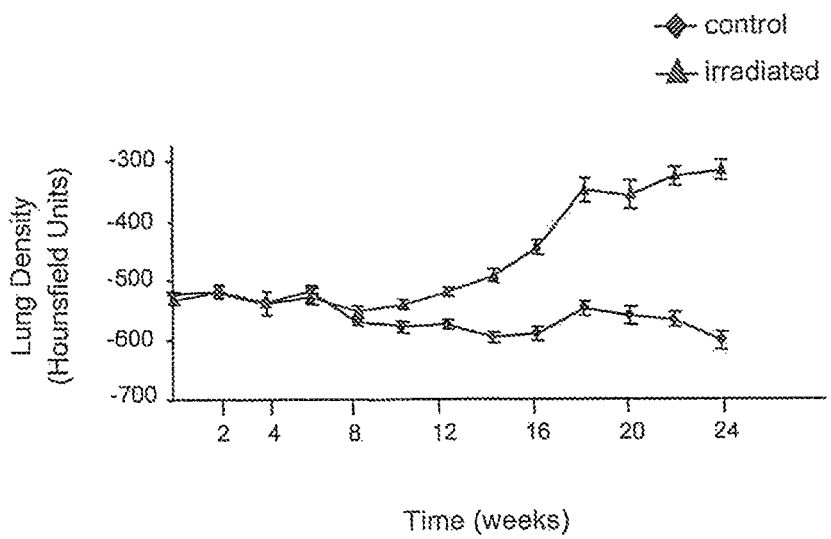

The later fibrogenesis phase is accompanied by a strong second onset of leukocyte infiltration that typically begins several weeks after irradiation and reaches a peak at about 20 weeks after irradiation. Development of fibrosis by progressive collagen deposition detectable by Masson's trichrome staining of irradiated lungs is usually evident after week 12. This fibrogenesis phase is characterized by development of typical fibroblast foci, with abnormal wound healing/repair leading to replication of mesenchymal cells, as characterized by fibroblast/myofibroblast migration and proliferation and exuberant deposition of extracellular matrix in irradiated lungs. At later time points (>20 wk), the fibroblast foci evolve and coalesce into more widespread fibrosis with remodeling of the lung architecture. The second onset of progressive fibrogenesis-related infiltration of leukocytes typically persists until the morphologically described fibrosis process is completed (after week 26). (See FIGS. 1B and 1C.) Fibrosis can be quantitatively assessed by measuring lung density (quantified in Hounsfield units, HU) using HRCT. Lung density dramatically increases during weeks 12-24 after radiotherapy in irradiated animals. (See FIG. 1D.)

Lung Remodeling Shown by Histology

To monitor the pathogenesis of the radiation-induced lung remodeling process and to evaluate the effects of CLN1, mice were selected for analysis of leukocyte infiltration and collagen deposition with associated thickening of the alveolar septum. Histological examination of H&E stained lung sections taken from mice at various time points after irradiation demonstrated that significant lung remodeling occurred between 13 and 19 weeks after irradiation in the irradiated but untreated mice, and administration of CLN1 attenuated this remodeling in a schedule-dependent manner in the mice treated with CLN1 (data not shown).

Potential Airspace

Figure 2A:
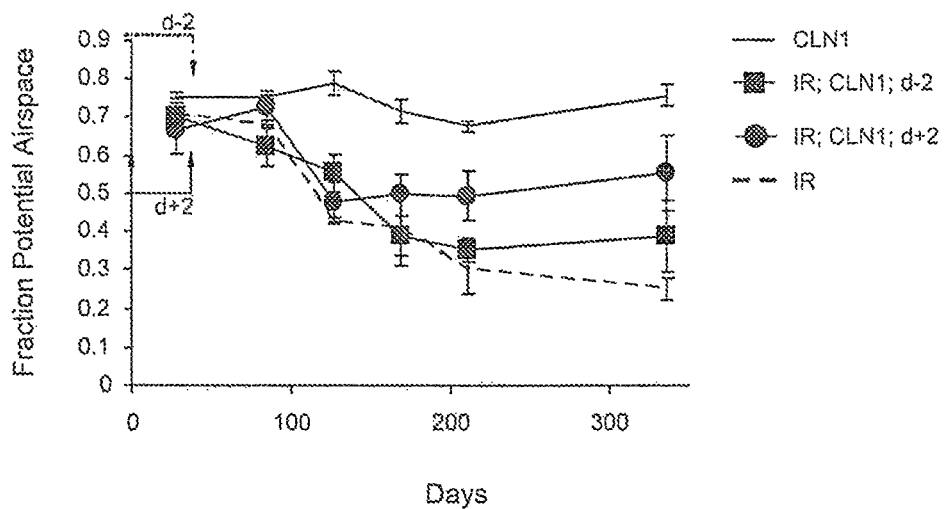
FIGS. 2A-2C set forth increased potential airspace in subjects treated with the methods and medicaments of the invention.
Figure 2B:
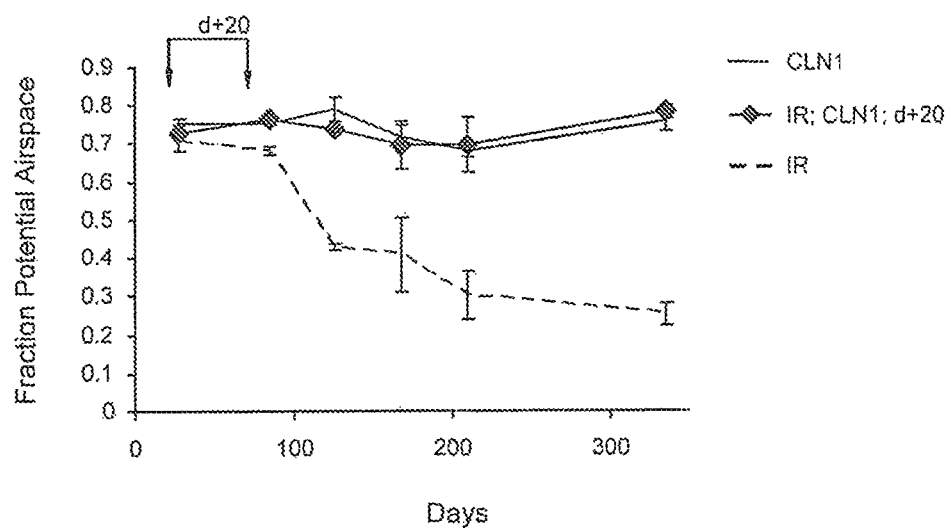
Figure 2C:
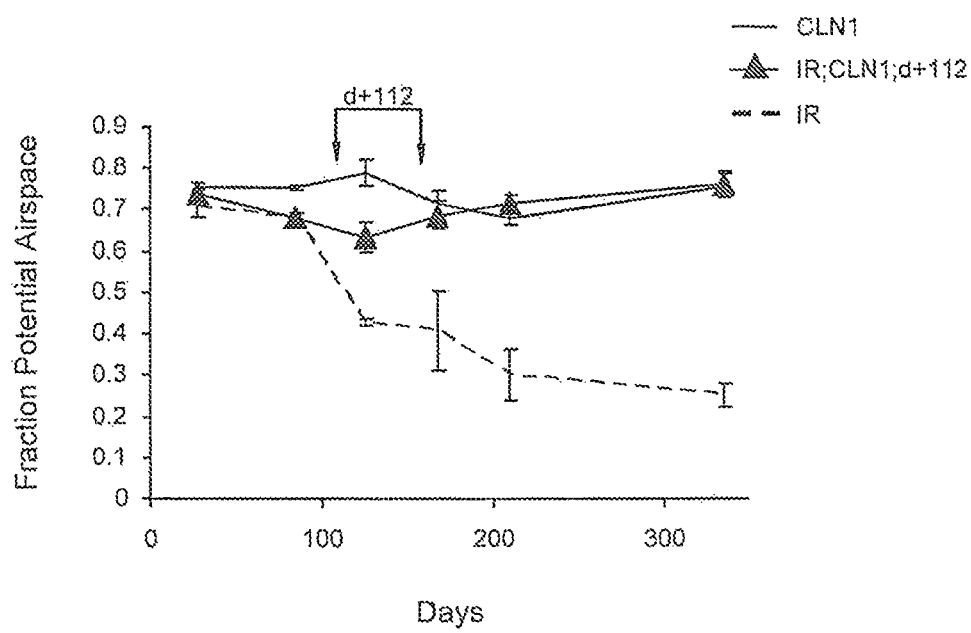

Evaluation of potential airspace in the lung, as assessed by image analysis of histological specimens, demonstrated that the present methods attenuate lung remodeling. (FIGS. 2A-2C) Image analysis of the H&E stained lung sections from the various groups were processed to quantify the amount of solid tissue vs. empty space. The ratio of empty space to tissue was called the fraction potential airspace. No significant change in potential airspace was observed in the first 12-13 weeks after irradiation in any of the groups. By week 19, however, the fraction potential airspace in the irradiated but untreated mice significantly decreased and continued to decrease until week 31. By week 31 after irradiation, all of the groups that had been treated with CLN1 exhibited larger fraction potential airspace than the irradiated untreated group. As shown in FIG. 2A, potential airspace in irradiated lungs improved when CLN1 administration was initiated 2 days before or 2 days after irradiation and continued for 8 weeks. As shown in FIGS. 2B and 2C, potential airspace in irradiated lungs was essentially normalized (that is, was very similar to the potential airspace seen in unirradiated mice) when CLN1 administration was initiated 20 days or even 112 days after irradiation, and treatment was continued for 8 weeks. Thus, the methods of the present invention reduce, reverse and even normalize lung remodeling in a subject having a radiation-induced pulmonary disorder.

Lung Density

Figure 3A:
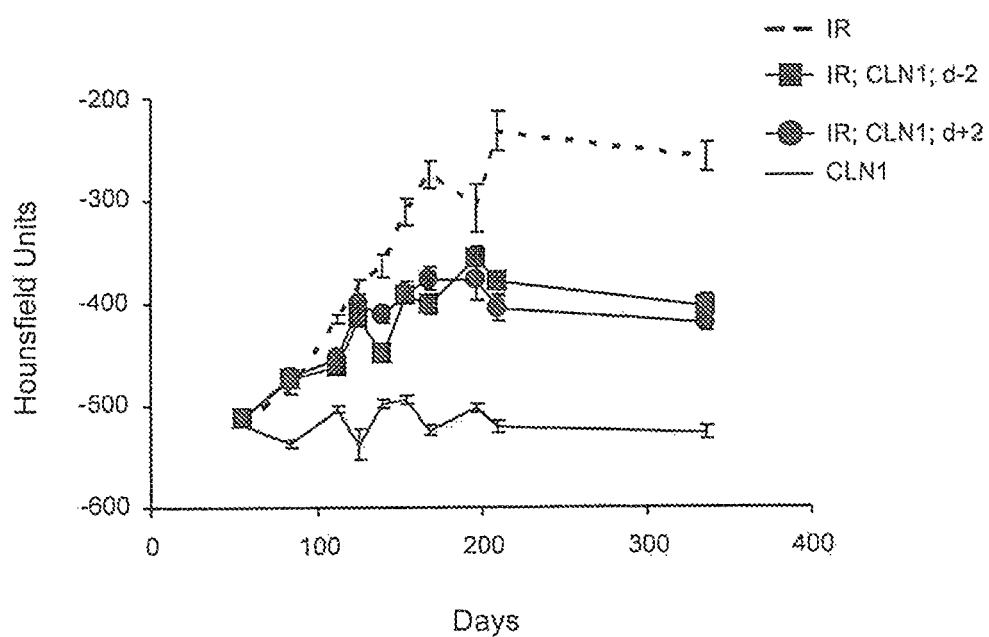
FIGS. 3A-3C set forth reduction, prevention, or reversal in increased lung density in subjects treated with the methods and medicaments of the invention.
Figure 3B:
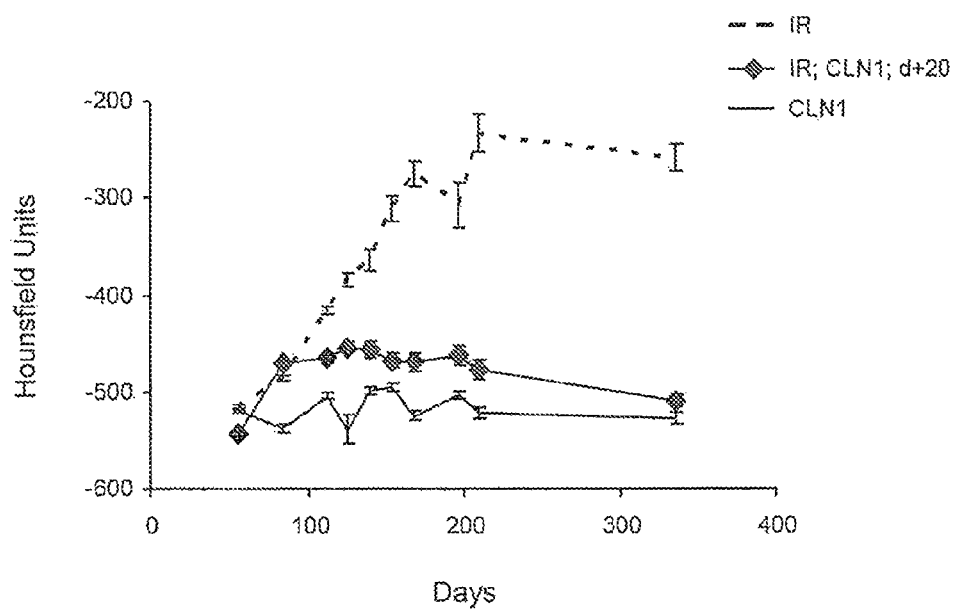
Figure 3C:
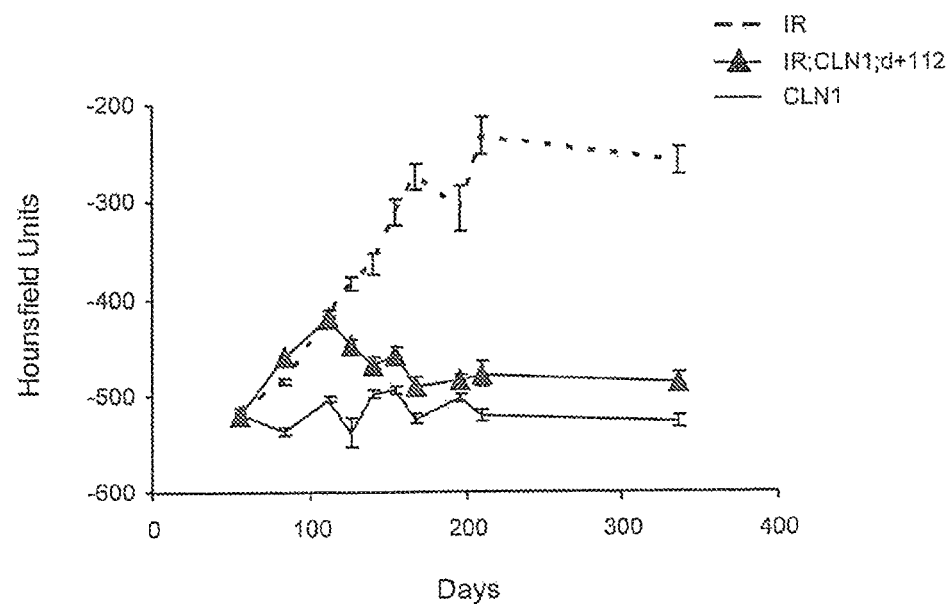

To monitor changes in lung density following irradiation and to evaluate the effects of CLN1 on the changes in lung density, the density of the lungs of all mice were measured by micro-CT at various times after irradiation. The density of the lungs of unirradiated mice (treated with either IgG or CLN1) was unchanged over the course of the experiment. In contrast, the lung densities in irradiated but untreated mice (either no treatment or treatment with IgG) progressively increased until about 30 weeks after irradiation, after which, the lung densities of the few surviving mice did not increase further. The changes in lung density observed in the irradiated but untreated mice were attenuated by the present methods when CLN1 was administered for 8 weeks beginning immediately before (d−2) or after (d+2) irradiation (FIG. 3A.) Administration of CLN1 beginning 20 days (d+20) or 112 days (d+112) after irradiation had a more dramatic effect on lung densities, such that the lung densities in the irradiated groups treated using the methods of the present invention were indistinguishable from those of unirradiated mice (FIGS. 3B and 3C) demonstrating the ability of an anti-CTGF agent to reverse and normalize a pathology associated with a lung remodeling disorder. Further, administration of CLN1 112 days after irradiation showed a reversal of lung density increases that occurred prior to treatment initiation (FIG. 3C.) Together, these data demonstrate that the methods of the invention are capable of reducing, reversing and normalizing the increased lung density that occurs in a subject having a radiation-induced pulmonary disorder.

Partial Pressure $O_2$ and Oxygen Saturation Percent

Figure 4A:
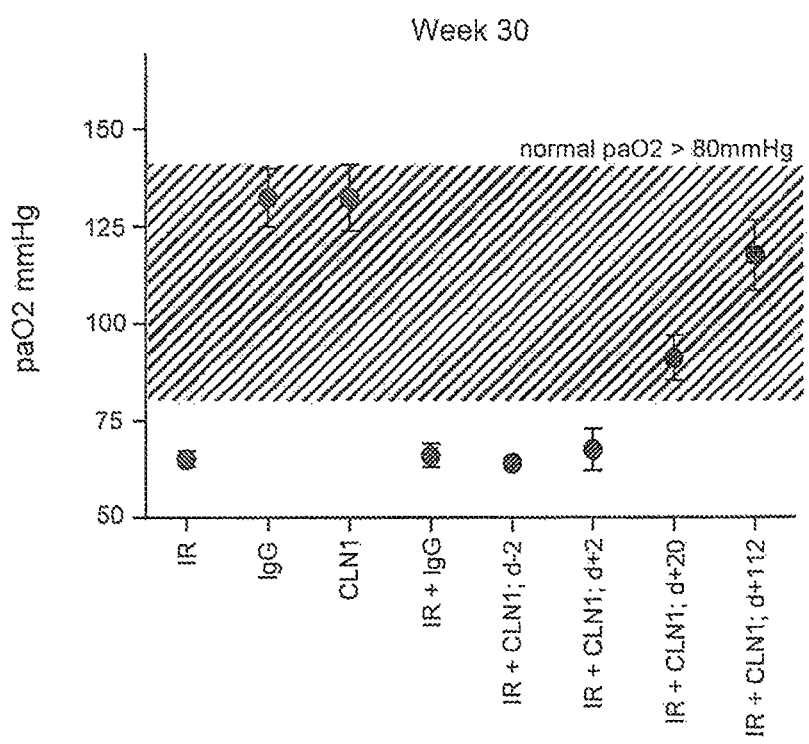
FIGS. 4A and 4B set forth improved blood gas parameters in subjects treated with the methods and medicaments of the invention.
Figure 4B:
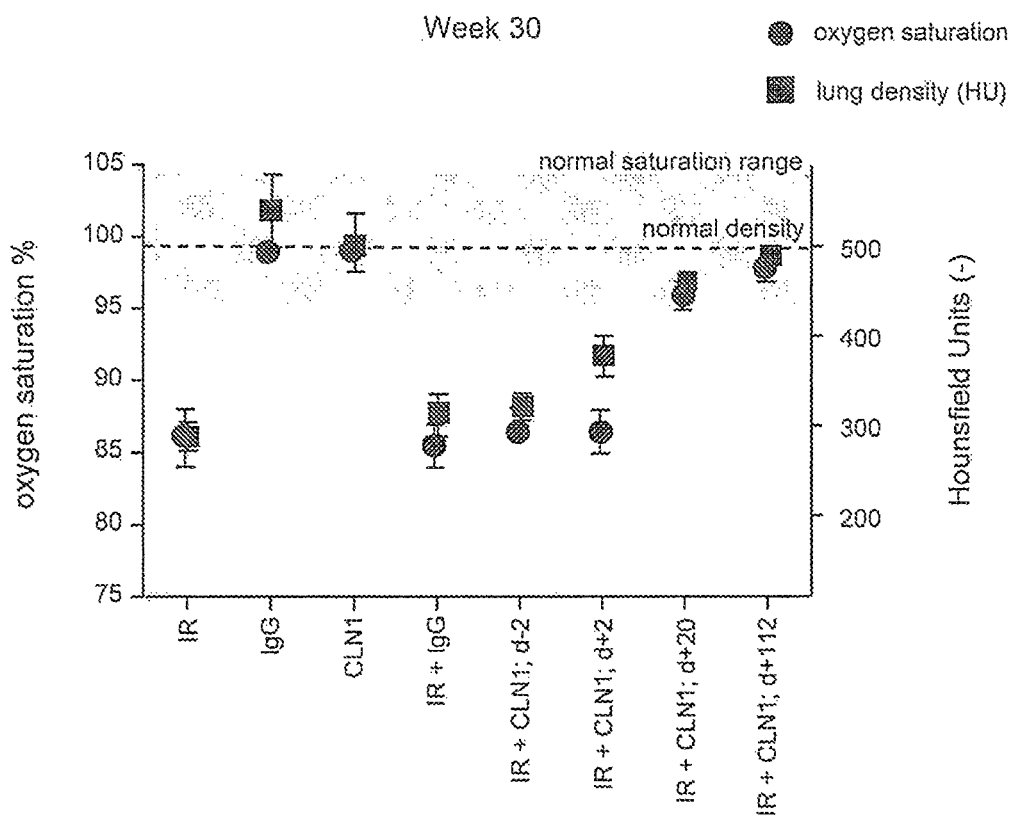

To monitor changes in lung function and to evaluate the effects of CLN1, blood was sampled from the tail capillary of mice in various groups and oxygen partial pressure was measured. FIGS. 4A and 4B set forth blood partial oxygen pressure ($PaO_2$) 30 weeks after irradiation for the treatment groups. The $PaO_2$ for mice in the unirradiated groups (IgG only or CLN1 only) was in the normal range (normal range is >80 mm Hg shown as the striped area). As can be seen in FIG. 4A, the irradiated but untreated mice (either no treatment or IgG treated) exhibited $PaO_2$ well below normal. However, irradiated mice that were treated with CLN1 beginning either at 20 days (d+20) or 112 days (d+112) after irradiation had $PaO_2$ in the normal range (FIG. 4A.) The oxygen partial pressure of the blood was converted to a percent saturation and compared to the lung densities measured at week 30 (FIG. 4B). As can be seen in FIG. 4B, the correlation of the lung density and the oxygen saturation is quite striking and suggested that reduction in lung density is a good surrogate for improvement in lung function, and both parameters are normalized in animals treated with the CLN1. Additional blood samples were collected at week 48 and measured for $PaO_2$ (data not shown). No mice remained alive in the irradiated untreated group at this time point but samples from 1-3 mice from the other groups were examined including remaining mice from the irradiated IgG treated group. Oxygen saturation was below normal in the irradiated IgG treated mice, but oxygen saturation was now in the normal range for all of the CLN1 treated groups demonstrating the ability of an anti-CTGF agent to increase oxygen saturation in a subject with a lung remodeling disease including normalizing oxygen saturation.

Septal Thickness

Another way to assess remodeling of the lungs is to measure the thickness of the septa between the alveoli. The thickness of the alveolar septa were measured manually from photographs of lung sections from mice in all groups. The mean of 100 measurements per lung section were plotted as a function of time (data not shown). Little change in the alveolar septa thickness was observed in the unirradiated mice. In contrast, the septa of irradiated and untreated (either no treatment or IgG treated) mice exhibited progressive thickening between 12 and 30 weeks after irradiation. Septa of irradiated mice that were treated with CLN1 beginning 2 days before or 2 days after irradiation also exhibited progressive thickening albeit with different time courses than the irradiated untreated controls. However, septa of irradiated mice that were treated with CLN1 beginning at 20 days or 112 days after irradiation exhibited little change in alveolar septa thickness (although there appeared to be a slight thickening at 12 weeks that subsequently resolved) and at 30 weeks after irradiation were indistinguishable from the unirradiated controls demonstrating that treatment with an anti-CTGF agent can prevent, reverse and normalize septal thickening associated with a lung remodeling disease.

Survival

Figure 5A:
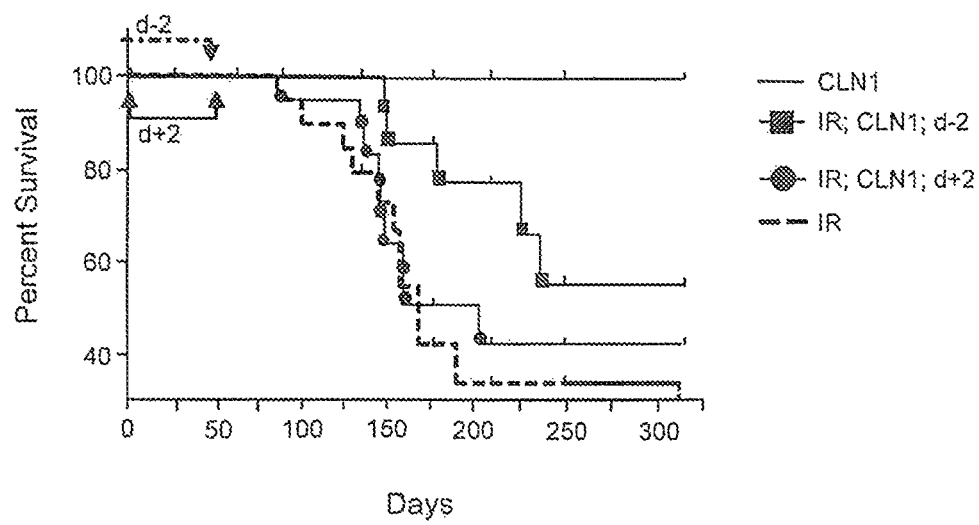
FIGS. 5A-5C set forth the survival rates in subjects treated with the methods and medicaments of the invention.
Figure 5B:
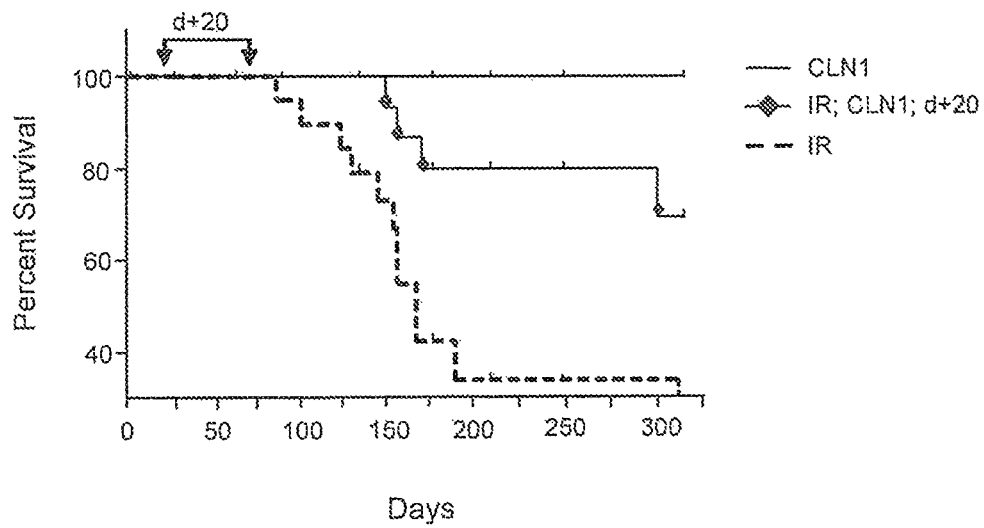
Figure 5C:
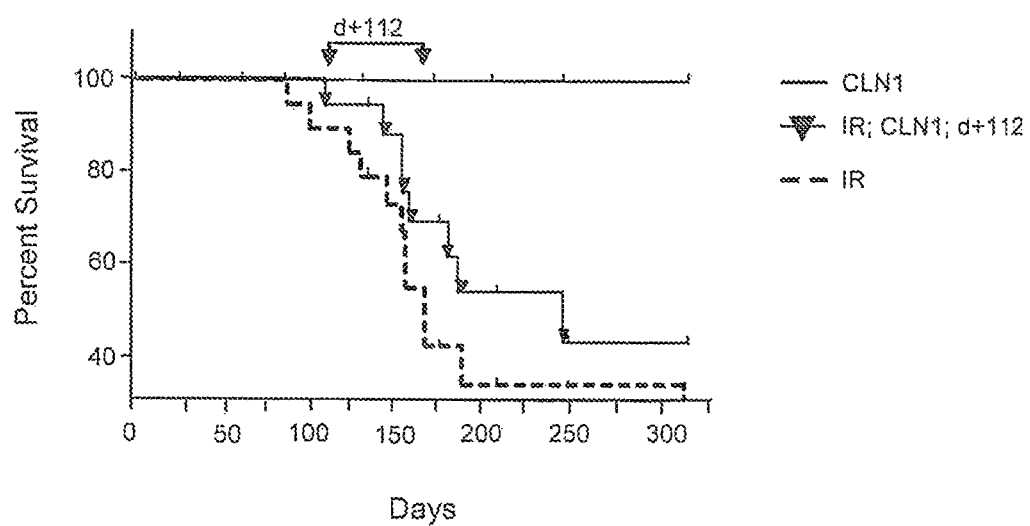

FIGS. 5A-5C show the percent survival of mice from treatment groups over the 48 weeks of the experiment. Over the course of the 48 week experiment, no mice in the unirradiated+CLN1 control group died, while one mouse in the unirradiated+IgG control group died (unirradiated+IgG group not shown on FIGS. 5A-5C). The survival of the irradiated and untreated mice (IR) and those that were irradiated and exposed to placebo (IR+IgG) were similar, with a median survival of 167 and 161 days, respectively (irradiated+IgG group not shown on FIGS. 5A-5C). The group that began receiving CLN1 two days before irradiation (d−2) exhibited a statistically significant improvement in survival (p=0.041) with a median survival >336 days (FIG. 5A) demonstrating that treatment with an anti-CTGF agent can extend survival by at least 200% compared to animals that do not receive an anti-CTGF agent. The group that began receiving CLN1 20 days after irradiation (d+20)

also exhibited a statistically significant improvement in survival relative to the irradiated placebo-treated group (p=0.021) with a median survival >336 days FIG. 5B) demonstrating that treatment with an anti-CTGF agent can extend survival by at least 200% compared to animals that do not receive an anti-CTGF agent. The group that began receiving CLN1 at 16 weeks after irradiation (d+112) exhibited an increase in median survival (246 days) over the irradiated untreated groups (FIG. 5C) demonstrating that treatment with an anti-CTGF agent can extend survival by at least 140% compared to animals that do not receive an anti-CTGF agent. The group that began receiving CLN1 2 days after irradiation (d+2) exhibited a median survival of 202 days (FIG. 5A) demonstrating that treatment with an anti-CTGF agent can extend survival by at least 120% compared to animals that do not receive an anti-CTGF agent. Thus all of the irradiated groups that received CLN1 treatment exhibited greater median survival rates after receiving a lethal ionizing radiation dose than the irradiated and untreated (or placebo treated) control groups. Together, these data demonstrate that the methods of the invention improve survivability and survival rate in a subject having a radiation-induced pulmonary disorder. In further embodiments, the methods of the invention improve the survival of subjects afflicted with a lung remodeling disease when treated with an anti-CTGF agent, thereby increasing the survival of the treated group by at least 5%, 10%, 15%, 20%, 25%, 30%, 35%, 40%, 50%, 60%, 65%, 70%, 75%, 80%, 90%, 100%, 125%, 150% or 200% compared to a control group not treated with the anti-CTGF agent.

Leukocyte Infiltration

The difference in survival between the group that began receiving CLN1 2 days before or 2 days after irradiation was unexpected, since their treatment periods almost completely overlapped, with less than 1 week difference between them. The acute response to irradiation is characterized by edema and leukocyte infiltration, and CTGF has the potential to alter either or both of these events. CTGF has been reported to modulate the motility of immune cells such as macrophages, suggesting that CLN1 could directly affect leukocyte infiltration. In addition, CTGF may alter secretion of chemokines and cytokines that recruit and maintain leukocytes. Therefore, CTGF may have direct and indirect effects on leukocyte infiltration that could be altered by the presence of CLN1 before irradiation. To test this hypothesis, the number of leukocytes infiltrating the lungs at 2 days after irradiation (see Plathow et al. (2004) *Invest. Radiol.* 39:600-609) was compared for the irradiated and untreated group (IR) and the group that was pretreated with CLN1 for 2 days prior to irradiation (d−2). A slightly smaller number of leukocytes per high power field were observed in lung slices from the CLN1-pretreated mice than from the irradiated, untreated mice (data not shown).

Leukocyte infiltration into the lungs of mice from all groups was also examined at 18 weeks after irradiation which corresponds to about the mid-point of the chronic response to irradiation. By 18 weeks, about 5 times the number of leukocytes was observed per field in the lungs of irradiated mice compared to unirradiated mice. Relative to irradiated and placebo-treated mice (IR+IgG), pretreatment of mice with CLN1 (d−2) decreased leukocyte infiltration by a small but statistically significant amount, while treatment with CLN1 beginning 2 days after irradiation (d+2) did not alter the number of leukocytes in the lungs at 18 weeks after administration. Administration of CLN1 beginning 20 days or 16 weeks (112 days) after irradiation demonstrated a greater inhibition of leukocyte infiltration into the lungs at 18 weeks after irradiation, such that it was indistinguishable from that of unirradiated mice demonstrating the ability of treatment with an anti-CTGF agent to prevent, reverse or normalize leukocyte infiltration associated with a lung remodeling disease.

Although the present examples were limited to 8 week treatment windows due to potential immune reaction in mice being treated with a human monoclonal antibody, the results clearly demonstrate that the methods provide significant improvement in all treatment periods. Thus, benefit can be seen in a subject whether the present methods are initiated prior to thoracic exposure to ionizing radiation or at times subsequent to exposure and even at times subsequent to the manifestation of acute or chronic effects of the radiation. The data clearly demonstrate that, to the extent possible, the methods should be initiated as early as possible and maintained throughout the period that the subject remains at risk for diminished organ function and compromised survivability. The data also clearly demonstrate that patients in the chronic progressive phase of the disorder can still benefit from the methods and medicaments of the present invention, improving lung function, reversing lung remodeling and improving survival.

Example 2

Human Lung Specimens

Paraffin embedded lung tissue sections prepared from autopsy specimens were obtained from 6 patients with BPD and 3 newborn patients without lung disease. The BPD patients were born between 23 to 28 weeks of gestational age and died between 2 to 11 months of chronological age. Diagnosis of BPD was made based on standardized criteria including oxygen requirement for more than 28 days at 36 weeks postmenstrual age (Jobe A H et al. *Am J Respir Crit Care Med.* 2001; 163: 1723-1729). The non-BPD patients born between 34 to 36 weeks of gestational age were diagnosed with trisomy 18, complex congenital heart disease and anencephaly and died within 2 to 6 h.

Examination of CTGF expression in lung tissue sections revealed that CTGF expression was dramatically increased in the thickening alveolar septa in BPD lungs as compared with the control lungs where CTGF expression was low. These data support a role of CTGF in the pathogenesis of BPD.

Example 3

Hyperoxia-Induced Lung Remodeling

The lungs of neonates and premature infants are often not sufficiently developed to oxygenate blood effectively. Consequently, these infants are treated with oxygen, in hyperbaric chambers, to keep the infants alive until they can survive in room air. However, even short term exposure to pure oxygen (or high concentration of oxygen) can be toxic or result in serious long-term effects, for example, pulmonary and cardiovascular remodeling. Exposure of the underdeveloped lungs to high oxygen concentrations may trigger pulmonary hypertension or cancers, and may affect organs beyond the lungs including kidney, heart, brain, eye, and vasculature.

CTGF was known to be elevated during neonatal hyperoxia (Chen et al. (2007) Pediatric Res. 62:128-133) and confirmed by Example 2, supra, but the functional significance of this is not completely understood.

Objective: To determine the effect of anti-CTGF antibody on prevention and treatment of hyperoxia-induced bronchopulmonary dysplasia in neonatal rats. The anti-CTGF antibody used in these experiments, Ab3149, is a rodent-specific chimeric antibody derived from the CLN1 antibody described herein, that was designed to eliminate the problem of mouse anti-human antibodies that can result when a human anti-CTGF antibody is used for experiments in mice or rats. Ab3149 contains the variable regions of the human CLN1 and the constant region of a mouse IgG2a, and is indistinguishable from CLN1 in binding to CTGF, but importantly, no rat anti-mouse antibodies were seen in rats after 15 weeks of dosing with Ab3149.

Study Design: Hyperoxia exposure and anti-CTGF antibody treatment: Within 24 h after birth Sprague Dawley rat pups were randomly allocated to receive room air (21% O2) or 90% O2. Continuous 90% O2 exposure was achieved in a Plexiglas chamber (77×64×37 cm) by a flow-through system. The oxygen level inside the Plexiglas chamber was monitored continuously with a Ceramatec (MAXO2) oxygen analyzer. Nursing dams were rotated between room air and hyperoxia every 24 h to prevent oxygen toxicity in the dams. The room air and hyperoxia groups were subdivided to receive Ab3149 (10 mg/kg) or placebo (control IgG) (20 mg/kg) i.p. injection. To prevent BPD, rat pups received Ab3149 or placebo on day 1 and then every other day during hyperoxia or room air exposure until sacrificed at day 14.

Lung histology and morphometry: On day 14, rat pups were sacrificed and lungs were pressure fixed for parafilm embedding and section. Lung tissue sections were stained by H&E for histology and morphometry. Lung morphometry was performed as previously described with some modification (Chen S et al. Am J Physiol Lung Cell Mol Physiol. 2011; 300(3):L330-40.). Briefly, 10 random non-overlapping images are taken under 20× magnification on three H&E stained tissue sections of every 100 μm distance from each lung by a research staff blind to experimental conditions. The large airways and blood vessels are excluded from the analysis. Quantification of mean linear intercept (MLI), radio alveolar count (RAC) and secondary septa were performed using MetaMorph Imaging System by an Analytical Imaging Core Facility member blind to experimental conditions. At least 8 animals were evaluated in each group (total 48).

Mean linear intercept (MLI), vascular density (VD) and medial wall thickness (MWT) of pulmonary arterioles were determined as a means of assessing the extent of pulmonary vascular remodeling. PH was determined by RVSP and RVH. β-catenin signaling was assessed by β-catenin nuclear translocation and cyclin D1 expression. Western blot analysis for CTGF expression was performed on lung homogenates using the method of Wu S et al. (Wu S et al. Am J Respir Cell Mol Biol 2010; 42:552-63). Lung gelatinolytic activity of matrix metalloproteinase-2 (MMP-2) was evaluated with zymography using the method of Fan W H et al. (Fan W H et al. J Biol Chem 2002; 277:9800-9805). Data were expressed as means t SD. Comparison among the groups was performed by one-way ANOVA followed by Student-Newman Keuls test. A P<0.05 was considered significant.

Results:

Treatment with an anti-CTGF agent improved alveolarization in the hyperoxia treated animals. The lungs from the hyperoxia+IgG treated animals had an increased MLI compared to the control (room air+IgG) animals. Treatment with Ab3149 reduced the increase in MLI of the hyperoxia treated animals. Stained lung sections from the hyperoxia+Ab3149 animals showed increased alveolarization compared to the lung sections from the hyperoxia+IgG animals. Treatment with Ab3149 was also associated with increased numbers of secondary septa (seen in the stained sections) in the hyperoxia treated animals as compared to the IgG treated hyperoxia animals, FIG. 6. This demonstrates that treatment of animals exposed to hyperoxia with an anti-CTGF agent can increase alveolarization. The hyperoxemic animals treated with Ab3149 also showed increased vascular density, had more normalized arterial wall thickness, showed improved pulmonary arterial hypertension, and showed reduced macrophage infiltration, compared to the IgG treated hyperoxemic animals.

Nuclear translocation of β-catenin was inhibited in the Ab3149 treated hyperoxemic animals compared to the IgG treated hyperoxemics and Ab3149 prevented the increase in cyclin D1 that was seen in the IgG treated hyperoxemic animals. The data is summarized in Table 4.

TABLE 4

|  | RA-IgG | O$_2$_IgG | RA-Ab3149 | O$_2$_Ab3149 |  |
| --- | --- | --- | --- | --- | --- |
| MLI | 42.2 ± 2.7 | 65.9 ± 8.4* | 36.8 ± 1.5 | 48.5 ± 4.3** | *p < 0.001, **p < 0.001 |
| VD | 8.8 ± 1.9 | 2.6 ± 0.2* | 8.6 ± 1 | 5.7 ± 0.7** | *p < 0.001, **p < 0.001 |
| MWT | 0.1 ± 0.02 | 0.2 ± 0.03* | 0.09 ± 0.01 | 0.18 ± 0.05** | *p < 0.001, **p = 0.002 |
| RVSP | 15 ± 3 | 28.9 ± 5* | 15 ± 1 | 22.8 ± 2** | *p < 0.001, **p = 0.001 |
| RVH | 0.3 ± 0.04 | 0.4 ± 0.1* | 0.3 ± 0.01 | 0.3 ± 0.04** | *p = 0.03, **p < 0.001 |
| β-catenin | 0.01 ± 0.01 | 0.35 ± 0.1* | 0.01 ± 0.01 | 0.07 ± 0.02** | *p < 0.001, **p < 0.001 |
| CD1 | 0.07 ± 0.02 | 2.04 ± 0.6* | 0.7 ± 0.2 | 0.6 ± 0.1** | *p = 0.001, **p = 0.002 |

MLI = Mean Linear Intercept
VD = Vascular Density
MWT = Medial Wall Thickness
RVSP = Right Ventricular Systolic Pressure
RVH = Right Ventricular Hypertrophy
N = 5~10/group, Mean ± SD,
*compare to RA-IgG,
**compare to O$_2$-IgG These experiments demonstrate that hyperoxia alters development of neonatal rat lungs. Hyperoxia decreased alveolarization and vascularization resulting in fewer, larger alveoli. Hyperoxia also induced cardiovascular remodeling, pulmonary artery wall thickening and RV hypertrophy, leading to pulmonary arterial hypertension. Hyperoxia also increased epithelial to mesenchymal transition (EMT) in the lung and hyperplasia.

Treatment with the anti-CTGF agent, Ab3149, improved the lung development in hyperoxemic animals for all of the parameters measured. MLI was significantly reduced in hyperoxemic animals treated with Ab3149 being about 74% the size of MLI of hyperoxemic animals treated with IgG. Treatment of hyperoxemic animals with an anti-CTGF agent significantly reduced right ventricular systolic pressure to about 79% and right ventricular hypertrophy to about 75% of the values seen in hyperoxemic animals treated with IgG demonstrating the ability of an anti-CTGF agent to reduce hyperoxia induced pulmonary vascular remodeling and thus attenuate pulmonary hypertension.

Figure 6:
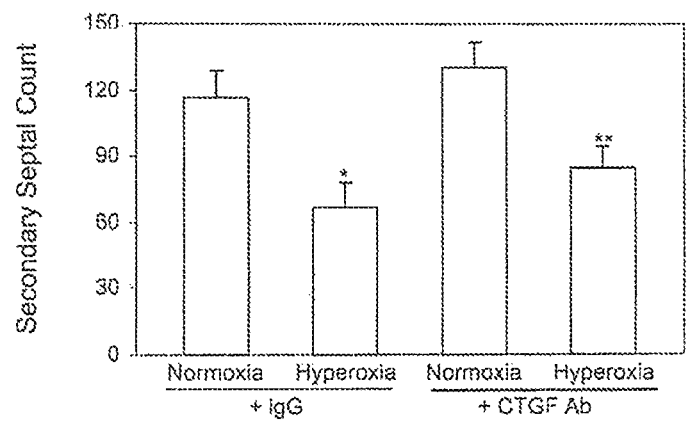
FIG. 6 illustrates the ability of an anti-CTGF antibody (Ab3149) to increase secondary septal count in animals exposed to hyperoxia. n=5/group. *$P<0.001$ and **$P<0.01$ compared to normoxia lungs.

Further, hyperoxemic animals treated with Ab3149 had increased secondary septa formation compared to hyperoxemic animals treated with IgG, FIG. 6. These facts demonstrate that treatment with an anti-CTGF agent improves alveolarization in neonatal rats exposed to hyperoxia.

Lung vascularization was increased by over 2-fold in hyperoxemic animals treated with an anti-CTGF agent compared to hyperoxemic animals treated with IgG demonstrating the ability of an anti-CTGF agent to increase vascular density.

Figure 7:
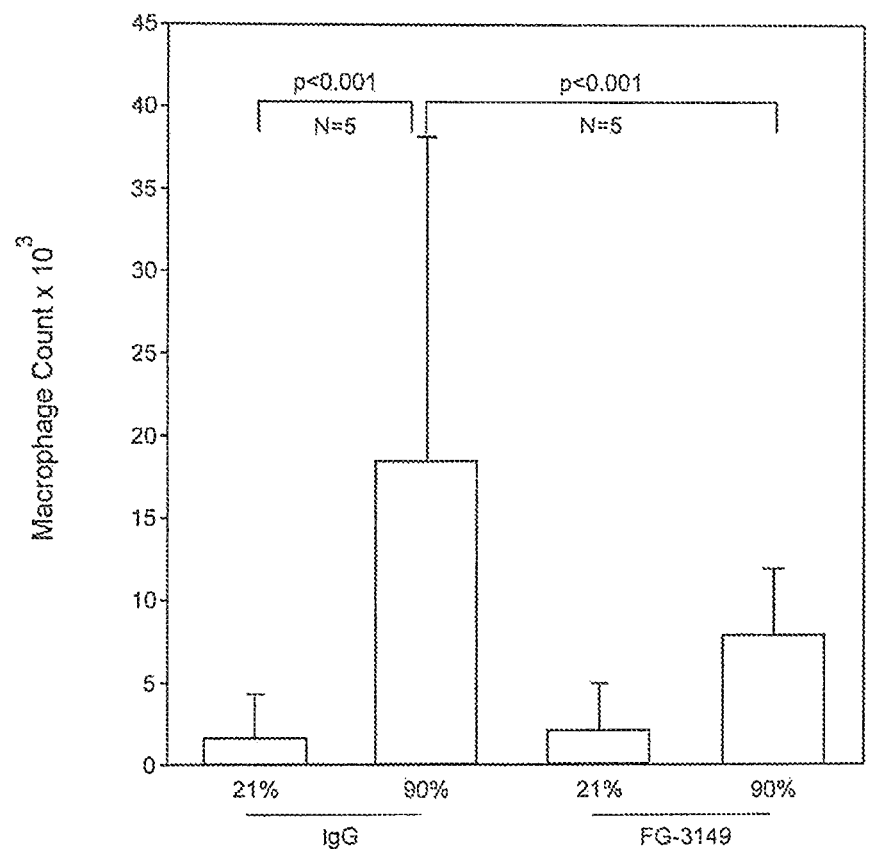
FIG. 7 illustrates the ability of an anti-CTGF antibody (Ab3149) to reduce the increase in lung macrophages induced by hyperoxia.

Additionally, treatment with an anti-CTGF agent significantly decreased macrophage infiltration into the alveoli of hyperoxemic animals compared to hyperoxemic animals treated with IgG, FIG. 7, indicating the ability of an anti-CTGF agent to decrease pulmonary inflammation.

MMP-2 is one of the major ECM-degrading protease that specifically degrades basement membranes and is known to play a role in systemic vascular remodeling. (See Galis Z S et al. *Circ Res* 2002; 90:251-262) Hyperoxia exposure was found to increase MMP-2 activity as evidenced by gelatin gel zymography. This activity was completely blocked by the anti-CTGF agent demonstrating the ability of an anti-CTGF agent to prevent increased expression of an ECM-degrading protease associated with lung tissue remodeling.

Example 4

Improvement in Lung Function of an Asthmatic

A 30-year-old patient is sent for reassessment of her asthma because her daily symptoms of cough and wheeze are not controlled on inhaled budesonide 400 µg bid. For control she requires treatment with salbutamol, two to three puffs daily. Her $FEV_1$ and slow vital capacity (SVC) are 2.0 L and 3.4 L (68% and 80% of predicted, respectively). Her $FEV_1$ improves to 2.5 L after inhaling 200 µg of salbutamol, confirming the presence of asthma. A sputum sample is taken for assessment of airway inflammation based on the measurement of sputum cell counts. The total cell count is 22 million cells/g (normal <9.7 million cells/g) of which 88% are neutrophils (normal <64.4%) and 5% are eosinophils (normal <2%). The sputum cell count indicates a combined infective and eosinophilic bronchitis. She is treated with an antibiotic and an anti-CTGF agent. Two months later, she no longer requires daily salbutamol, her $FEV_1$ is improved to 2.6 L presalbutamol representing a 30% improvement over baseline, and sputum total cell count and composition return to normal.

Example 5

Improvement in Lung Function of an Asthmatic Smoker

A 175-cm tall man that smokes and has asthma has an $FEV_1$ of 1.99 L. The average $FEV_1$ for a man of his age that does not smoke or have asthma is 3.05 L. Treatment with an anti-CTGF agent is initiated. At a later period, the man's lung function is tested again and the $FEV_1$ is found to improve to 2.4 L, demonstrating over a 20% increase from his baseline measurement.

Example 6

Improvement in Lung Function of COPD Patient

An elderly man suspected of having the emphysema phenotype of COPD is tested for baseline inspiratory capacity and arterial oxygen tension ($PaO_2$) values. His $FEV_1$ value is 1.17 L that is 48.3% of the predicted value for his age and height. His $FEV_1$/FVC is 45.1%, FRC is 120.9% of predicted, his RV is 191% of predicted, TLC is 120% of predicted and his $PaO_2$ is 65.1. These results confirm the suspected diagnosis of the emphysema phenotype of COPD.

The patient is treated with an anti-CTGF agent. At a later time period, the patient is retested for inspiratory capacity and $PaO_2$. His $FEV_1$ value is now 1.45 L, representing an over 20% increase compared to the baseline measurement. His $PaO_2$ value has risen to 69.3 representing an increase of over 6% from his initial baseline value. Further, his RV is reduced by over 10% demonstrating the ability of an anti-CTGF agent to improve the lung function and blood oxygenation of a patient with COPD.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed:

1. A method of increasing pulmonary alveolarization in a premature infant or neonate with bronchopulmonary dysplasia, the method comprising:
   administering to the premature infant or neonate an effective amount of an anti-connective tissue growth factor (anti-CTGF) antibody, thereby increasing pulmonary alveolarization in the premature infant or neonate, wherein the anti-CTGF antibody has the same amino acid sequence as the antibody produced by the cell line identified by ATCC Accession No. PTA-6006 and wherein the anti-CTGF antibody is administered at a dose of at least 20 mg/kg.

2. The method of claim 1, wherein the anti-CTGF antibody is administered systemically.

3. The method of claim 1, wherein the anti-CTGF antibody is administered by aerosolization or nebulization.

4. The method of claim 1, further comprising administering an additional therapeutic agent selected from the group consisting of corticosteroids, bronchodilators, anticholinergics, vasodilators, diuretics, anti-hypertensive agents, acetazolamide, antibiotics, immunosuppressive drugs, surfactants and supplemental oxygen.

* * * * *